Figure 1A:
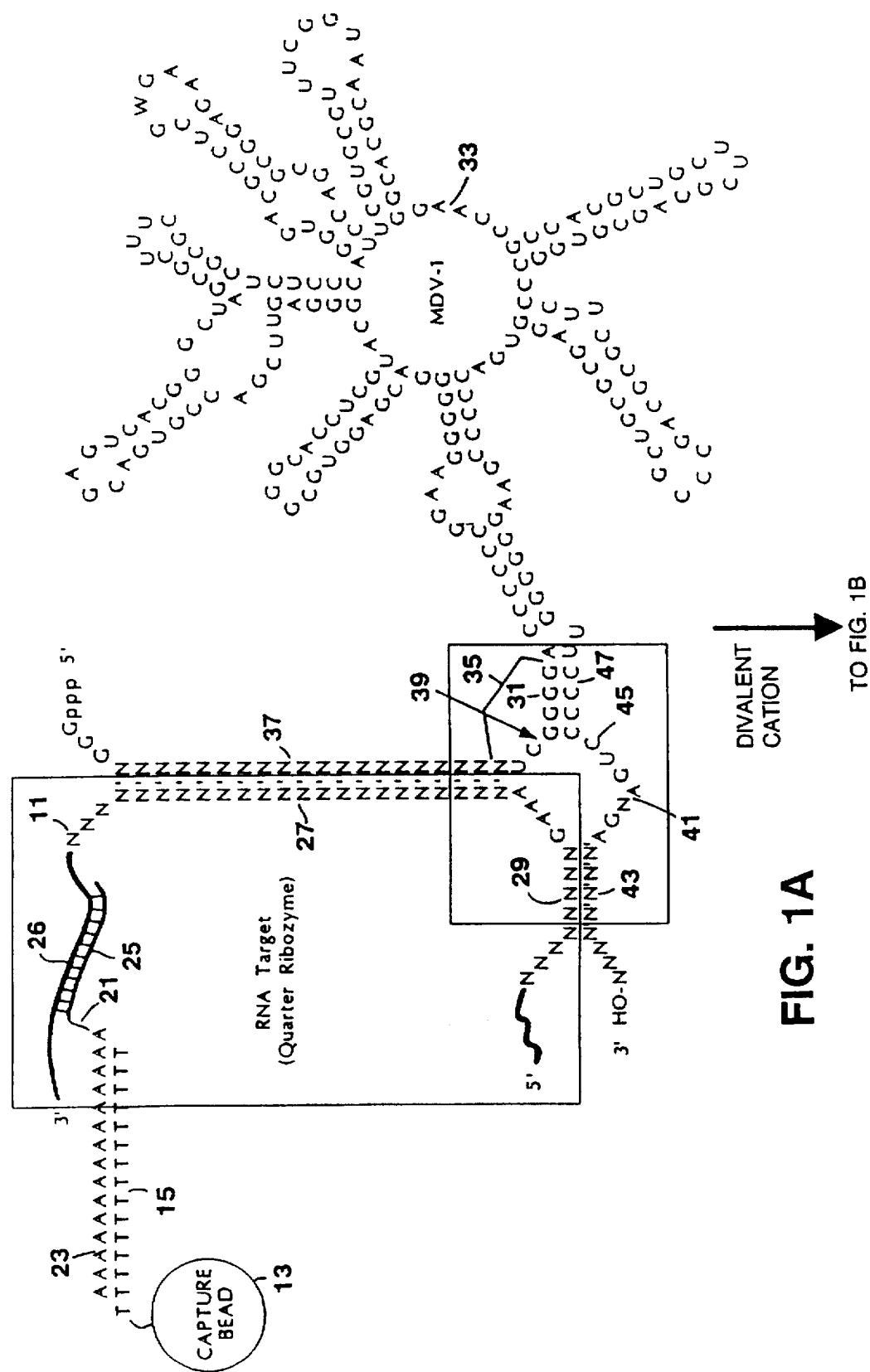

United States Patent [19]

Stefano

[11] Patent Number: 5,763,171

[45] Date of Patent: *Jun. 9, 1998

[54] NUCLEIC ACID STRUCTURES WITH CATALYTIC AND AUTOCATALYTIC REPLICATING FEATURES AND METHODS OF USE

[75] Inventor: James Ernest Stefano, Hopkinton, Mass.

[73] Assignee: Amoco Corporation, Chicago, Ill.

[*] Notice: The term of this patent shall not extend beyond the expiration date of Pat. No. 5,472,840.

[21] Appl. No.: 468,049

[22] Filed: Jun. 6, 1995

Related U.S. Application Data

[63] Continuation of Ser. No. 630,288, Dec. 17, 1990, Pat. No. 5,472,840, which is a continuation-in-part of Ser. No. 252,243, Sep. 30, 1988, abandoned, and a continuation-in-part of Ser. No. 370,218, Jun. 22, 1989, abandoned.

[51] Int. Cl.$^6$ .............................. C12Q 1/68; C12P 19/34; C12N 15/11
[52] U.S. Cl. .................. 435/6; 435/91.1; 435/91.21; 435/91.3; 536/23.1; 536/24.3
[58] Field of Search ................. 435/6, 91.1, 91.21, 435/91.3; 536/23.1, 24.3

[56] References Cited

U.S. PATENT DOCUMENTS

| | | | |
|---|---|---|---|
| 4,786,600 | 11/1988 | Kramer et al. | 435/235 |
| 4,957,858 | 9/1990 | Chu et al. | 435/6 |
| 5,472,840 | 12/1995 | Stefano | 435/6 |

FOREIGN PATENT DOCUMENTS

| | | | |
|---|---|---|---|
| WO 87/06270 | 10/1987 | WIPO . | |
| WO 90/03446 | 4/1990 | WIPO . | |

OTHER PUBLICATIONS

Hill et al., Does QB–replicase synthesize RNA in the absence of template, Nature, vol. 301, pp. 350–352, Jan. 1993.

Mills et al., Nucleotide sequences of microvariant RNA: Another small replicating molecule, Proc. Natl. Acad. Sci., vol. 72(11), pp. 4252–4256, Nov. 1975.

Hampel and Tritz, A Model for the RNA Catalyzed Cleavage of a Plant Satellite RNA, J. Cell. Biochem. Supplement 12D, Abstract N 212, p. 31, 1988.

Hampel et al., 'Hairpin' Catalytic RNA Model: Evidence for Helices and Sequence Requirement for Substrate RNA, Nucleic Acids Research 18: 299–304, 1990.

Haseloff et al., Simple RNA Enzymes With New and Highly Specific Endoribonuclease Activities, Nature 334: 585–591, 1988.

Mills et al., Complete Nucleotide Sequence of a Replicating RNA Molecule, Science 180: 916–927, 1973.

Ruffner et al., Sequence Requirements of the Hammerhead RNA Self–Cleavage Reaction, Biochemistry 29:10695–10702, 1990.

Forster et al., Self–Cleavage of Virusoid RNA is Performed by the Proposed 55–Nucleotide Active Site, Cell 50:9–16, 1987.

Uhlenbeck, A Small Catalytic Oligoribonucleotide, Nature 328:596–600, 1987.

Syvänen et al., Fast Quantification of Nucleic Acid Hybrids by Affinity-basd Hybrid Collection, Nucleic Acids Research 14:5037–5048, 1986.

Nishihara et al., Localization of the Qβ Replicase Site in MDV-1 RNA, J. Biochem. 93:669–674, 1983.

Kramer and Lizardi, Replicatable RNA Reporters, Nature 339:401–403, 1989.

Lizardi et al., Exponential Amplification of Recombinant-–RNA Hybridization Probes, Bio/Technology 6:1197–1202, 1988.

*Primary Examiner*—John L. LeGuyader
*Assistant Examiner*—Andrew Wang
*Attorney, Agent, or Firm*—Norval B. Galloway

[57] ABSTRACT

Methods and compositions are described for making ribozymes which can release or activate molecules including autocatalytically replicatable RNA such as MDV-1.

21 Claims, 8 Drawing Sheets

NUCLEIC ACID STRUCTURES WITH CATALYTIC AND AUTOCATALYTIC REPLICATING FEATURES AND METHODS OF USE

RELATED APPLICATIONS

This is a continuation of application Ser. No. 630,288, filed Dec. 17, 1990, now U.S. Pat. No. 5,472,840, which is a Continuation-In-Part application of two applications, U.S. Ser. No. 252,243, filed Sep. 30, 1988, now abandoned, and U.S. Ser. No. 370,218, filed Jun. 22, 1989, now abandoned.

Field of the Invention

This application relates to compositions, methods and processes for the delivery of inactive molecules to activation sites for therapeutic and diagnostic applications. In particular, one aspect of the invention features an RNA molecule which can be activated under controlled conditions. A further aspect of the invention features a RNA molecule which has a probe section and an autocatalytically replicatable section, and its diagnostic and therapeutic applications.

BACKGROUND OF THE INVENTION

The following definitions are provided to facilitate an understanding of the present invention.

The term "target" or "target molecule" in a diagnostic sense, refers to a molecule of interest, i.e. the molecule whose presence one wishes to know. In a therapeutic sense, the term "target" or "target molecule" refers to a molecule associated with a disease.

The term "biological binding pair" as used in the present application refers to any pair of molecules which exhibit mutual affinity or binding capacity. A biological binding pair is capable of forming a complex under binding conditions. For the purposes of the present application, the term "ligand" will refer to one molecule of the biological binding pair, and the term "antiligand" or "receptor" will refer to the opposite molecule of the biological binding pair. For example, without limitation, embodiments of the present invention have application in nucleic acid hybridization assays where the biological binding pair includes two complementary nucleic acids. One of the nucleic acids is designated the ligand and the other nucleic acid is designated the antiligand or receptor. One of the nucleic acids may also be a target molecule. The designation of ligand or antiligand is a matter of arbitrary convenience. The biological binding pair may include antigens and antibodies, drugs and drug receptor sites, and enzymes and enzyme substrates, to name a few.

The term "probe" refers to a ligand of known qualities capable of selectively binding to a target antiligand or receptor. As applied to nucleic acids, the term "probe" refers to nucleic acid having a base sequence complementary to a target nucleic acid. The probe and the target are capable of forming a probe target complex under binding conditions. The term "probe" will be used herein, in both a diagnostic sense, meaning capable of binding a molecule, the presence or absence of which one desires to know, and a therapeutic sense, capable of binding to a molecule associated with a disease.

The term "label" refers to a chemical moiety which is capable of detection including, by way of example, without limitation, radioactive isotopes, enzymes, luminescent agents, precipitating agents, and dyes. The term "agent" is used in a broad sense, including any chemical moiety which participates in reactions which lead to a detectable response. The term "cofactor" is used broadly to include any chemical moiety which participates in reactions with the label.

The term "active" and "inactive" are used in a relative sense. The term "active" suggests normal or optimal chemical biological activity or reactiveness, and also encompasses such biological activity or reactiveness which, although less than normal or optimal, is greater than some other level of activity or reactiveness. The term "inactive" suggests exhibiting less biological activity or reactiveness than active.

The term "amplify" is used in the broad sense to mean creating an amplification product, which may include by way of example, additional target molecules, or target-like molecules, capable of functioning in a manner like the target molecule, or a molecule subject to detection steps in place of the target molecule, which molecules are created by virtue of the presence of the target molecule in the sample. In the situation where the target is a polynucleotide, additional target, or target-like molecules, or molecules subject to detection can be made enzymatically with DNA or RNA polymerases.

The term "ribozyme" refers to an RNA structure of one or more RNAs having catalytic properties. Ribozymes generally exhibit endonuclease, ligase or polymerase activity.

The term "contiguous" means an adjacent area of a molecule. By way of example, in the case of biological binding pairs, where a first ligand binds to a receptor target molecule, the area surrounding and adjacent to the first ligand is open and capable of binding to a second ligand contiguous to the first. In the context of nucleic acid, where a first probe binds to an area of a larger nucleic acid target molecule, an adjacent mutually exclusive area along the length of the target molecule can bind to a second probe which will then be contiguous to the first. The target molecule acts as a template, directing the position of the first probe and the second probe. The term "substantially contiguous" is used in the functional sense to include spatial orientations which may not touch, may not abut, or may overlap, yet function to bring parts, areas, segments and the like into cooperating relationship.

The term "autocatalytically replicatable" refers to enzymatically catalyzed, self-directed replication of the type characterized by several RNAs and RNA enzymes. By way of example the enzyme, RNA-dependent RNA polymerase, of the bacteriophage Q-Beta (Q-Beta replicase), under reaction conditions, will act on a 221 nucleotide RNA template, known generally as midivariant-1 (MDV-1), and variations of MDV-1, including without limitation, minivariant RNA, microvariant RNA, nanovariant RNA, and modifications thereof to produce many copies of the RNA template. Other enzymes which participate in autocatalytic replication processes are, without limitation, SP replicase and MS2 replicase.

The term "capture ligand" means a ligand capable of specifically binding with a capture antiligand associated with a support.

The term "retrievable support" is used in a broad sense to describe an entity which can be substantially dispersed within a medium and removed or separated from the medium by immobilization, filtering, partitioning, or the like.

The term "support," when used alone, includes conventional supports such as filters and membranes as well as retrievable supports.

The term "reversible," in regard to the binding of ligands and antiligands, means capable of binding or releasing upon imposing changes which do not permanently alter the gross chemical nature of the ligand and antiligand. For example, without limitation, reversible binding would include such binding and release controlled by changes in pH, temperature, and ionic strength which do not destroy the ligand or antiligand.

Genetic information is stored in living cells in thread-like molecules of DNA. In vivo, the DNA molecule is a double helix of two complementary strands of DNA, each strand of which is a chain of nucleotides. Each nucleotide is characterized by one of four bases: adenine (A), guanine (G), thymine (T), and cytosine (C). The bases are complementary in the sense that, due to the orientation of functional groups, certain base pairs attract and bond to each other through hydrogen bonding and π-stacking interactions. Adenine in one strand of DNA pairs with thymine in an opposing complementary strand. Guanine in one strand of DNA pairs with cytosine in an opposing complementary strand. In RNA, the thymine base is replaced by uracil (U) which pairs with adenine in an opposing complementary strand. The genetic code of a living organism is carried upon the DNA strand, in the sequence of base pairs.

Molecules of DNA consist of covalently linked chains of deoxyribonucleotides and molecules of RNA consist of covalently linked chains of ribonucleotides. Each nucleic acid is linked by a phosphodiester bridge between the 5'-hydroxyl group of the sugar of one nucleotide and the 3'-hydroxyl group of the sugar of an adjacent nucleotide. The terminal ends of nucleic acid are often referred to as being 5'-termini or 3'-termini in reference to the terminal functional group. Complementary strands of DNA and RNA form antiparallel complexes in which the 3'-terminal end of one strand is oriented and bound to the 5'-terminal end of the opposing strand.

Nucleic acid hybridization assays are based on the tendency of two nucleic acid strands to pair at their complementary regions to form hybrids. The formation of such hybrids can be made to be highly specific by adjustment of the conditions (sometimes referred to as stringency) under which this hybridization takes place such that hybridization will not occur unless the sequences are precisely complementary. If total nucleic acid from the sample is immobilized on a solid support such as a nitrocellulose membrane, the presence of a specific "target" sequence in the sample can be determined by the binding of a complementary nucleic acid "probe" which bears a label. After removal of non-hybridized probe by washing the support, the amount of target is determined by the amount of detectable moiety present.

The identification of unique DNA or RNA sequences or specific genes within the total DNA or RNA extracted from tissue or culture samples, may indicate the presence of physiological or pathological conditions. In particular, the identification of unique DNA or RNA sequences or specific genes, within the total DNA or RNA extracted from human or animal tissue, may indicate the presence of genetic diseases or conditions such as sickle cell anemia, tissue compatibility, cancer and precancerous states, or bacterial or viral infections. The identification of unique DNA or RNA sequences or specific genes within the total DNA or RNA extracted from bacterial cultures may indicate the presence of antibiotic resistance, toxicants, viral- or plasmid-born conditions, or provide identification between types of bacteria. Thus, nucleic acid hybridization assays have great potential in the diagnosis and detection of disease. Further potential exists in agriculture and food processing where nucleic acid hybridization assays may be used to detect plant pathogenesis or toxicant-producing bacteria.

However, the sensitivity of such assays is limited by the number of labelled moieties which one may physically incorporate into the probe nucleic acid. In the case of radioactively-labelled probes, the practical limit of deletion is about $10^4$ target molecules. To achieve this sensitivity requires probes with radioactive labels which have a very high energy and a very limited useful lifetime. The detection step, autoradiography, requires several days. Other labelling methods utilizing fluorescent, chemiluminescent, or enzymatic detection, although more rapid, usually do not exceed the sensitivity of radioactively-labelled probes. Since most organisms of clinical interest do not contain more than 50,000 copies of any nucleic acid suitable for use as a target, the utility of such methods is restricted to the detection of large numbers of organisms. The level of infectious agents in clinical specimens or foodstuffs, however, often does not exceed one to ten organisms.

One approach for the detection of low levels of DNA utilizes a DNA-dependent DNA polymerase to directly replicate the DNA target to increase its numbers to easily detectable levels. This approach is termed "polymerase chain reaction" (PCR). Saiki, R. K., Scharf, S., Faloona, F., Mullis, K. B., Horn, G. T., Erlich, H. A., and Arnheim, N., "Enzymatic Amplification of Beta-globin Genomic Sequences and Restriction Site Analysis for Diagnosis of Sickle Cell Anemia," Science 230:1350–1354 (1985); Saiki, R. K., Gelfand, D. H., Stoffel, S., Scharf, S. J., Higuchi, R., Horn, G. T., Mullis, K. B., and Erlich, H. A., "Primer-directed Enzymatic Amplification of DNA with a Thermo-stable DNA Polymerase," Science 239:487–491 (1988); Erlich, H. A., Gelfand, D. H., and Salki, R. K., "Specific DNA Amplification": Nature 331:461- (1988) and Mullis et al., European Patent application Nos. 200362 and 201184 (see also U.S. Pat. Nos. 4,683,195 and 4,683,202).

In practice, PCR is limited by the requirement that the target for amplification be DNA (as opposed to RNA), and by the occurrence of false positives generated by hybridization of probes to homologous sites in non-target DNA which fortuitously generate similar replication products. Moreover, although target DNA may be detected with very high sensitivity, the numbers of targets present in the sample is difficult to determine without adding significantly to the complexity of the assay. Since the number of infectious agents is often important in evaluating the treatment protocol for disease, this amplification approach is disadvantageously limited because it provides qualitative rather than quantitative results.

Another approach to improving the sensitivity of nucleic acid detection is to employ a nucleic acid probe associated with an autocatalytically replicatable RNA molecule. As used herein, the word "associated" means linked to or incorporated within. For example, a number of means to generate RNA probes by derivatizing MDV-1 RNA, a template for Qβ replicase, are suggested by Chu, B. C. F., Kramer, F. R., and Orgel, L. E., "Synthesis of an Amplifiable Reporter RNA for Bioassays", Nucl. Acids Res. 14: 5591–5603 (1986); Lizardi, P. M., Guerra, C. E., Lomeli, H., Tussie-Lune, I, and Kramer, F. R., "Exponential Amplification of Recombinant-RNA Hybridization Probes", Bio/Technology 6:1197–1203 (October, 1988); and European Patent Application 266,399 (EP Application No. 87903131, 8).

An autocatalytically replicatable RNA-probe construct may be employed in a sandwich hybridization assay, such as that described by Ranki, et al., U.S. Pat. No. 4,563,419; Soderlund, G. B., U.S. Pat. No. 2,169,403; Stabinsky, U.S. Pat. No. 4,751,177; and Syvanenen, et al., Nucl. Acids Res.

14:5037-5048. In the event the target is present and probe has hybridized to target, the autocatalytically replicatable RNA associated with the probe is replicated to generate amounts of RNA which may be easily detected by a variety of means (for example, by fluorescence using a dye such as ethidium bromide or propidium iodide). Since the MDV-1 RNA template for Qβ replicase is doubled in number every 20 seconds in vitro, an exponential increase (estimated to be a billion-fold) in the number of RNA molecules occurs within a few minutes at a single temperature. The autocatalytic reaction proceeds at an exponential rate until the number of autocatalytically replicatable RNA molecules exceeds the number of active enzyme molecules in the reactions. After that point, the amount of autocatalytically replicatable RNA increases linearly with time. As a consequence, in reactions given a sufficient period of time to reach this linear phase (for example 15 minutes for 100 molecules), the amount of amplified product RNA will be directly related to the logarithm of the number of autocatalytically replicatable RNAs initially added (Lizardi et al., supra). Since the initial number of autocatalytically replicatable RNA probes is proportional to the amount of target, the amount of target present in the sample being examined may be quantitated over a very wide range.

Autocatalytic replicatable RNA probe constructs have been suggested in the art. In one approach, the probe is coupled to the RNA via a cystamine moiety containing a disulfide (—S—S—) linkage which can be cleaved prior to replication (Chu et al., supra). However, this method suffers from the need for several synthesis steps that increase the cost in labor of producing such probes. In addition, disulfide linkages are subject to premature cleavage by reducing agents (for example, glutathione) which occur naturally in many biological samples.

In another approach, the probe sequence may be incorporated within the sequence of the replicatable RNA (Lizardi et al., supra). However, the probe sequence is viewed as foreign by the enzyme and affects the ability of the RNA to be efficiently replicated, or is spontaneously deleted during replication. Deletion events affect the rate of replication and occur randomly with time. When deletion events occur, the level of the RNA products obtained in the linear phase of the amplification cannot be used to assess target level.

Linking the probe sequence to either the 3' or 5' termini of autocatalytically reproducible RNAs via the phosphodiester linkage normally found in RNAs, although simple to accomplish by a variety of means, has been reported to strongly inhibit replication. For example, ligation of a short oligoribonucleotide, $A_{10}$, to the 5' nucleotide of MDV-1 RNA rendered the RNA unable to replicate exponentially (Miele, Ph.D. thesis, Columbia University, 1982). Attachment of additional nucleotides to the 3' terminus of other autocatalytically reproducible RNAs similarly inhibits their replication by Qβ replicase. For example, addition of between 10-20 cytidylate residues to the 3' terminus of Qβ phage RNA abolishes its template activity (Gillis, E., Devos, R. and Seurinck-Opsomer, C., Arch. Int. Physiol. Biochem. 84:392-393 (1976)); addition of a short oligoadenylate tract has a similar effect (Gilvarg, C., Jockusch, H. and Weissmann, C., Biochim. Biophys. Acta 414, 313-8 (1975); see also Devos, R., van-Emmelo, J., Seurinck-Opsomer, C., Gillis, E., and Fiers, W., Biochim. Clophys. Acta. 447:319-27 (1976)). Chu et al. in WO 87/06270 suggest, that attachment of an affinity molecule might be possible to autocatalytically reproducible RNA provided it is done through a purine linkage. The purine linkage would be subjected to an acid depurination cleavage procedure prior to replication. The clear implication of the Chu application, which is consistent with all the other teachings in the art, is that the autocatalytically reproducible RNA bearing terminally added sequences is inactive until cleaved.

The discussion thus far has focused on signal generation. Signal generation which is related to the presence of target is very desirable. Signal generation which is not related to target, referred to as background, is undesirable. By way of example, a single autocatalytically replicatable RNA molecule in the presence of Q-Beta replicase and reaction conditions, will initiate the production of copies at an exponential rate. In the event such single autocatalytically replicatable RNA is associated with a probe, which probe is bound to target, the exponential replication is a true positive detection. In the event such single autocatalytically replicatable RNA is not associated with a probe, or if associated with a probe and such probe is not associated with target, the exponential replication is a false positive or constitutes background from which true signal must be differentiated. The presence of background limits the sensitivity of assays at low target concentrations. Target induced signal must be significantly greater than background in order for assays to be considered reliable.

One form of background, in affinity assays, occurs when the probe having a label associates with molecules other than target, and is carried through to detection. This type of background is often associated with non-specific binding of probe to supports.

One approach to reducing this non-specific binding background employs a method by which the target-probe complex is reversibly bound to the support ("reversible target capture"). After hybridization and immobilization, the complex is eluted from the support, which is then discarded with the non-specifically bound probe. The target-probe is then recaptured on fresh support. This process may be repeated several times to produce a significant reduction in the amount of non-hybridized probe (see Collins, European Patent Application No. 87309308.2).

A further type of background, common with autocatalytic replicatable amplification systems, is "unprimed" activity of the enzyme itself. Prior to the advent of purified Q-beta replicase, it was believed that the enzyme inherently had the capability to create MDV-1, without a template.

In a therapeutic sense, the ability to activate nucleic acid in a controlled manner is useful to control the expression of genes or to remove cells which harbor infection. By way of example, the control of viral genes with antisense molecules can prevent viruses from replication. In the alternative, cells which harbor viruses can be poisoned by autocatalytically replicating RNA to prevent viruses from infecting other cells.

The inability to control the amplification of autocatalytically replicatable molecules for diagnostic and therapeutic purposes has limited the application of such technology.

SUMMARY OF THE INVENTION

The present invention features means for the control and amplification of autocatalytically replicatable molecules for diagnostic and therapeutic purposes. One embodiment of the present invention features a composition of matter. The composition of matter comprises a first nucleic acid having a first section and a second section. The first section is capable of autocatalytic replication under reaction conditions as part of the first nucleic acid, which includes the second section. The second section, positioned at one of the ends of the first section, is capable of assuming a bound position with a target.

In describing nucleic acids, the terms "sections," "parts," "areas," "segments," and the like, are used in reference to one or more nucleotides forming part of the nucleic acid molecule. Such sections, parts, areas, segments and the like may be contiguous, or may overlap, or may be separated by nucleotides which are not necessary for the functions being described herein.

Preferably, the composition includes a first nucleic acid which is RNA, and in particular a first section which has sequences which are substantially identical to MDV-1. As used herein, the term substantially identical to MDV-1 means that such sequences are capable of autocatalytic replication in the presence of the enzyme of Q-beta replicase. Preferably, the sections are connected 5' end to 3' end, or 3' end to 5' end, as opposed to 3' end to 3' end, or 5' end to 5' end, to facilitate manufacture and making of the RNA, by oligonucleotide synthesis and through cloning.

A further embodiment of the present invention features a first nucleic acid having an inhibitory element and a first section, and a second section. The first section is capable of active autocatalytic replication under reaction conditions when the first section is separated from the inhibitory element and is inactive when such first section is part of the first nucleic acid integral with the inhibitory element. The second section has sequences which are capable of interacting with release means to separate the first section from the inhibitory element. The first nucleic acid is capable of assuming a bound position with a target, in which said second section is capable of interacting with release means.

The inhibitory element may take several forms. Indeed, one embodiment features a first nucleic acid having a third section which by virtue of being part of the first nucleic acid extending either alone or with other sections renders such first section inactive.

In this context, it is useful to note, that the autocatalytic replication activity of the MDV-1 sequences which are part of a larger nucleic acid, with 3' or 5' terminal associated section may be less than optimal for an MDV-1 molecule. However, where an enzyme, Q-beta replicase, having no endogenous activity is used, such less-than-optimal activity is capable of being discerned from background. Similar structures are used in methods of the present invention which feature separation of a first section from other sections of a nucleic acid. Such methods featuring such separation suggest that the first section is inactive, even though a similar structure is capable of autocatalytic replication. Cleavage or separation increases the activity of MDV-1 like sequences by as much as 100,000 fold. Such differences in activity can be readily perceived.

A further embodiment features-ligand and antiligand systems as inhibitory elements for inactivating the first section of the first nucleic acid. By way of example, ligands which are capable of binding to or interacting with the first section of the first nucleic acid may be capable of rendering the first section incapable of autocatalytic replication. Inhibitory elements utilizing ligand systems allow activation to occur following a cleavage event as a result of the destablization of the binding of the ligand system to the MDV-1 like sequences or activation may be due to the release of the first section to the extent that it is able to assume an active tertiary structure, or activation may be due to interactions with the enzyme. Inhibitory elements for inactivating the first section may include ligands and antiligand systems such as biotin-avidin or complementary nucleic acid sequences positioned in cooperating relationship on the first nucleic acid, antibody-antigen interactions and protein binding interactions.

One embodiment of the present invention features nucleotide sequences which are capable of interacting with the first section, rendering the first section inactive. One embodiment features sequences capable of interacting with MDV-1 like sequences in the first section in approximately the 81 to 126 MDV-1 nucleotide region. The interaction may include binding directly to the region but is not necessarily limited to such binding. The interaction may also include shielding the region from Interaction with the enzyme Q-beta replicase, interfering with the enzyme, and distorting the tertiary structure of the region. A preferred sequence of nucleotides Includes the nucleotides 5'-UUYRC-3'(SEQ ID NO:1), where Y represents any pyrimidine nucleotide and R is any purine nucleotide. One embodiment features inhibitory sequences wherein Y is U and R is A.

Release means may take several forms. Any of a number of nucleases may be advantageously employed as release means. For example, micrococcal nuclease may be used since it does not cleave MDV-1 RNA (Hill & Blumenthal (1983) Nature 301, 350–352). Corey & Schultz (1987) Science 238:1401–1403, teach the construction of such oligonucleotide-micrococcal nuclease conjugates. Any number of ribozymes with endonucleolytic cleavage activity, such as those described by Haselhoff & Gerlach (Nature 3343:585–591 (1988)). Uhlenbeck (1987) Nature 328, 596–600, Cech (European Pat. Appl. WO 88/04300, June 1988), Sharmeen et al. (1989) J. Virol. 63, 1428–1430; or Hampel & Tritz (1988) J. Cell. Biochem., Suppl. 12D, Abst. #N212, p.31, may be employed.

In the specific case where the target is RNA, release means may be a small DNA oligonucleotide (for example, six nucleotides) complementary to a portion of the second section sequence of the first nucleic acid. In this case, the cleavage is ideally effected by the addition of RNase H (which acts to cleave RNA in RNA:DNA heteroduplexes) to the solution in contact with the support bearing the complex. Naturally, the means for capturing the RNA target should ideally avoid generation of such heteroduplexes in order for the cleavage event to be specific. For example, a biotinylated RNA complementary to another portion of the target RNA may be conveniently captured upon an immobilized streptavidin support.

In the specific case where the target is DNA, digestion of the sequence extension of hybrids with target may be effected directly by the addition of RNase H, without the requirement for a second probe bearing such an oligonucleotide.

Ribozymes possess a significant advantage in that the probes bearing the ribozyme may be efficiently produced in a single step by transcription of a DNA oligonucleotide of appropriate sequence such as is described by Miligan (supra), thus reducing the cost and labor required to generate such reagents. Moreover, ribozymes tend to produce specific cleavage events, leading to a product RNA with defined replication properties.

One embodiment of the present invention features release means in the form of a ribozyme formed with a first nucleic acid. The first nucleic acid has first section, a second section and an inhibitory element. The first and second sections are as described above, and the inhibitory element comprises a nucleic acid which renders the first section inactive. The first nucleic acid further has a fourth section which fourth section is positioned at one of the ends of the first section opposite the second section. The fourth section cooperates with the second section to form a ribozyme. In the presence of ribozyme reaction conditions, the first section is separated from the inhibitory element of the first nucleic acid, allowing the first section to become active. Preferably, the second section of the first nucleic acid includes a cleavage site.

In one embodiment, the fourth section and second section require the presence of target which contributes nucleic acid sequences to form the ribozyme. The requirement for specific sequences in the target to form a ribozyme facilitates a further reduction in background. Signal can not be generated without target.

One such structure is described by the Formula I below:

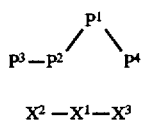

Formula I

As used above, the letter X generally represents target, and $X^1$ represents a first target region having one or more nucleotides which form a ribozyme with the first nucleic acid, $X^2$ represents a terminal nucleotide of $X^1$ or a second target region and $X^3$ represents a terminal nucleotide of $X^1$ or a third target region. The letter P generally represents the first nucleic acid, and $P^1$ represents a first section, which section is capable of active autocatalytic replication when the first section is separated from an inhibitory element and inactive when the inhibitory element is integral with the first nucleic acid, in the presence of autocatalytic reaction conditions. The letter $P^2$ represents a second section of first nucleic acid, which section contributes one or more nucleotides to form a ribozyme. The letter $P^3$ represents an inhibitory element associated with the first nucleic acid. The letter $P^4$ represents a fourth section capable of contributing one or more nucleotides to form a ribozyme.

In one embodiment which features a structure which resembles a "hammerhead" ribozyme, $X^1$ and $P^4$ are mutually exclusive and comprise one of the group of sequences 5'-MGAAAK-3'(SEQ ID NO:2), and 5'-J'CUGANGAM'-3' (SEQ ID NO:3). $P^2$ comprises the sequences 5'-K'UWJ-3' (SEQ ID NO: 4), wherein the letter N represents a nucleotide selected from the group of nucleotides comprising A, G, U and C. The letter W represents C or A. The letters J, J', K, K', M and M' each represent four or more nucleotides. The nucleotides of J and J', are complementary, as are the nucleotides of K and K' and the nucleotides of M and M'. Such complementarity is believed to provide stability and alignments for the ribozyme structure. Complementarity among nucleotide groups within sections and areas of the same nucleic acid, such as K' and J of second section $P^2$, J' and M' of fourth section $P^4$, allows such sections to form "stem" loops which open only on interaction with target, rendering such first nucleic acid incapable of forming ribozyme structures without specific target interaction. Such groups of nucleotides may also incorporate inhibitory sequences which interact with the first section.

The inhibitory element, $P^3$, can be any moiety capable of inhibiting autocatalytic replication. Preferably, the inhibitory element is a nucleic acid. In which case, $P^3$ can be any sequence of nucleotides. However, for diagnostic and therapeutic purposes, it is useful to have greater specificity to target than the sequences of M, M', K and K' may provide. The inhibitory sequences can be sequences capable of assuming a bound position to target at target region $X^1$.

A further embodiment of the present invention features a first nucleic acid and a second nucleic acid which in the bound position to target form a ribozyme. One such structure is described by the Formula II below:

Formula II

As used above, the letter X generally represents target, $X^1$ represents a first target region, and $X^2$ represents a terminal nucleotide of $X^1$ or a second target region, and $X^3$ represents a terminal nucleotide of $X^1$ or a third target region. The letter P generally represents the first nucleic acid. $P^1$ represents the first section which section is capable of active autocatalytic replication when the first section is separated from the inhibitory element and inactive when the inhibitory element is integral with the first nucleic acid and first section, in the presence of autocatalytic reaction conditions. The letter $P^2$ represents a second section having one or more nucleotides which are capable of participating ribozyme formation. The letter $P^3$ represents an inhibitory element. The letter $P^4$ represents a terminal nucleotide of $P^1$ or a fourth section capable of contributing sequences which participate in ribozyme formation with $P^2$ and $R^1$. As used above, the letter R generally represents the second nucleic acid, and $R^1$ represents a first area capable of having one or more nucleotides which participate in ribozyme formation. The letter $R^2$ represents a terminal nucleotide of $R^1$ or represents a second area of the second nucleic acid capable of assuming a bound position with respect to target region $X^1$. At least one of $R^1$, $R^2$, $P^2$, $P^3$, are capable of assuming a bound position with target.

In one embodiment, the structure formed resembles a "hammerhead" ribozyme. In which case, the letter $P^2$ represents the sequence, 5'-K'UWJ-3' (SEQ ID NO:4), $X^1$ and $R^1$ are mutually exclusive and represent one of the group of sequences 5'-MGAAAK-3' (SEQ ID NO:2), and 5'-J'CUGANGAM'-3' (SEQ ID NO: 3), wherein N is one of the nucleotides U, G, A and C. The letter W represents C or A. The letters J, J', K, K', M and M' each represent four or more nucleotides. The nucleotides of J and J' are complementary as are the nucleotides of K and K' and the nucleotides of M and M'. $P^4$ is a terminal nucleotide of $P^1$.

Complementarity between nucleotide groups within an area or section, such as K' and J of second section $P^2$, and J' and M' of first area $R^1$, allows such sections and areas to form "stem" loops which open up only on interaction with target, rendering such first nucleic acid incapable of forming a ribozyme structure without specific target interaction. Such areas may also incorporate inhibitory sequences which interact with the first section.

In a further embodiment, $P^2$, represents the sequence, 5'-K'UWJ-3', and $P^4$ and $R^1$ are mutually exclusive and selected from the group of sequences 5'-MGAAAK-3' (SEQ ID NO:2) and 5'-J'CUGANGAM'-3' (SEQ ID NO:3), or $R^1$ includes both groups of sequences and $P^4$ is the terminal nucleotide of $P^1$. The letters W, J, J', K, K', M, M', and N are as described immediately above. At least one of $R^2$, and $P^3$ are capable of forming a bound position at $X^1$, $X^2$, and $X^3$.

In one embodiment, the structure formed resembles a "hairpin" ribozyme. In which case, $P^2$ represents the sequences 5'-FNGUCQ-3' (SEQ ID NO:5). The area represented by $R^1$ comprises the sequences 5'-Q'AGAAF'ACCA-GAGAAACACACGUUGUGGUAUAUUACCUGGUA-3' (SEQ ID NO:6). At least one of $R^2$ and $P^3$ are capable of assuming a bound position to target at $X^1$, $X^2$ or $X^3$. The letter Q and Q', F and F' each represent four or more nucleotides. The letter N represents one of the nucleotides U, G, A, C. The nucleotides of Q and Q' are complementary, as are the nucleotides of F and F'. At least one of $P^3$ or $R^2$ are capable of assuming a bound position to target. The inhibitory element binding at target region $X^3$ and the second area of the second nucleic acid assuming a bound position at target region $X^2$.

Complementarity between nucleotide groups within an area or section, such as F and Q of second section $P^2$, and F' and Q' of first area R', allows such sections and areas to form "stem" loops which open up only on interacting with target, rendering such first and second nucleic acids incapable of forming a ribozyme without specific target interaction. Such areas may also incorporate inhibitory sequences which interact with the first section.

As described with respect to Formula I, and now with respect to Formula II, greater specificity is obtained for target where the inhibitory element $P^3$ is capable of assuming a bound position with target. In systems described with respect to Formula II, utilizing a first nucleic acid and a second nucleic acid, greater specificity can be obtained where $R^2$ is capable of assuming a bound position with target.

The characteristic inability of the autocatalytically replicatable sequences to replicate efficiently until associated probes are specifically bound to target has led to descriptions of such compositions, as applied in diagnostics, as "smart probes." Smart probes provide reduction in background because they produce less or no signal until bound to target.

Compositions of the present invention have features of smart probes. Such smart probes have application in diagnostics, and can be used in conjunction with a variety of methods for background reduction such as sandwich assays and reversible target capture. However, the inherent low background of the compositions of the present invention may allow the compositions to be used in systems without a sandwich format and without reversible target capture.

One composition of the present invention features a first nucleic acid having a first section, and a second section, and inhibitory element and a support means. Each section has a 5' end and a 3' end. The support means is capable of binding to a support or is associated with a support. The first section is capable of active autocatalytic replication when the first section is separated from the inhibitory element and is inactive when the inhibitory element is associated with the first section. The inhibitory element is associated with the first section through the second section. The second section is capable of forming a ribozyme in the presence of target, which ribozyme cleaves the first section from the ligand under ribozyme reaction conditions.

An embodiment of the composition is described by Formula III below:

Formula III

As used above, the letter X generally represents target, $X^1$ represents a first region, and $X^2$ represents the terminal nucleotide of $X^1$ or $X^2$ represents a second region, $X^3$ represents the terminal nucleotide of $X^1$ or represents a third target region. The letter P generally represents a first nucleic acid, $P^1$ represents a first section capable of active autocatalytic replication when the first section is separated from the inhibitory element, and inactive when integral with the inhibitory element. The letter $P^2$ represents a second section capable of forming a ribozyme in the presence of the target. The letter $P^3$ represents an inhibitory element such as, without limitation, nucleotide sequences capable of interaction with the first section, or such nucleotides which by virtue of their number, inhibit autocatalytic replication. The letter $P^4$ represents the terminal nucleotide of the first section $P^1$, or represents a fourth section-capable of participating in the formation of a ribozyme. Support means, generally represented by the letter S, is any conventional or retrievable support, or a ligand capable of binding to such support. Support means may constitute inhibitory element, or inhibitory element may be part of support means.

One embodiment, which features a ribozyme which resembles "hammerhead" structure, $P^2$ represents the sequences 5'-K'UWJ-3' (SEQ ID NO:4), $X^1$ and $P^4$ are mutually exclusive and are selected from the groups of sequences 5'-MGAAAK-3' (SEQ ID NO:2) and 5'-J'CUGANGAM'-3' (SEQ ID NO:3), wherein N is one of the bases U, G, A, and C. The letter W represents C or A. The letters J, J', K, K', M and M' each represent four or more nucleotides. The nucleotides of J and J' are complementary, as are the nucleotides of K and K', and the nucleotides of M and M'.

The composition may also comprise a second nucleic acid which cooperates with the first nucleic acid to form a ribozyme in the presence of target. Such a composition is described by the Formula IV set forth below:

Formula IV

As used above, the letters $X^1$, $X^2$, $X^3$, S, $P^4$, $P^3$, $P^2$ and $P^1$ are consistent with the description immediately above. The letter R generally represents a second nucleic acid having a first area and a second area. The first area represented by the letter $R^1$, is capable of forming a ribozyme with the second section $P^2$ of the first nucleic acid. The letter $P^4$ represents the terminal nucleotide of $P^1$ or represents a fourth section to which contributes sequences to form a ribozyme. The second section is represented by the letter $R^2$, is the terminal nucleotide of $R^1$ or represents an area of the second nucleic acid capable assuming a bound position to the target at $X^3$.

In one embodiment which resembles a "hairpin" ribozyme, $P^2$ represents the nucleotide sequences 5'-FNGUCQ-3' (SEQ ID NO:5), R represents the nucleotide sequences 5'-Q'AGAAF'ACCAGAGAAACACACGUUGUGGUAUAUUACC UGGUA-3' (SEQ ID NO:6). The letters Q, Q', F and F' each represent four or more nucleotides. The nucleotides of Q and Q' are complementary as are the nucleotides of F and F. $P^4$ is the terminal nucleotide of $P^1$. At least one of the sections or areas of the first nucleic acid and second nucleic acid are capable of assuming a bound position. The second area of the second nucleic acid assuming a bound position at target third region $X^3$ and inhibitory element $P^3$ assuming a bound position with target at target second region $X^2$.

In one embodiment, which features a structure which resembles a "hammerhead" ribozyme, $P^2$ represents the sequences 5'-K'UWJ-3' (SEQ ID NO:4), $X^1$ and $R^1$ are mutually exclusive and represent one of the groups of sequences 5'-MGAAAK-3' (SEQ ID NO:2) and 5'-J'CUGANGAM'-3-40 (SEQ ID NO:3), wherein N is one of the bases U, G, A and C. The letter N represents C or A. The letters J, J', K, K', M and M' each represent four nucleotides. The nucleotides of J and J' are complementary, as are the nucleotides of K and K' and the nucleotides of M and M'. $P^4$ is the terminal nucleotide of $P^1$.

In a further embodiment, $P^2$, represents the sequence, 5'-K'UWJ-3' (SEQ ID NO:4), and $P^4$ and $R^1$ are mutually exclusive and selected from the group of sequences 5'-MGAAAK-3' (SEQ ID NO:2) and 5'-J'CUGANGAM'-3' (SEQ ID NO:3), or $R^1$ includes both groups of sequences and $P^4$ is the terminal nucleotide of $P^1$. The letters W, J, J', K, K', M, M', and N are as described immediately above. At least one of $R^2$ and $P^3$ are capable of forming a bound position at $X^1$, $X^2$ and $X^3$.

The support means in formulas III and IV allows the target nucleic acid complex to be separated from debris, reagents, and other nucleic acid which may be present in the sample. The first section of the first nucleic acid is inactive, unless in the presence of target it is separated or cleaved, minimizing or eliminating background.

By way of example, support means may include a biotin group for capture upon a support derivatized with avidin or streptavidin, a fluorescein group for capture upon a support bearing immobilized antibodies to fluorescein, a poly A tail for capture upon a support bearing immobilized oligo or poly dT and a binding site for the coat protein of bacteriophage R17 for capture upon a support bearing the coat protein.

A number of means may be employed to associate a ligand with the first nucleic acid. By way of example, where the support means is 3' to the site of cleavage, biotin, fluorescein, proteins, antibodies and antigens may be associated by one of several methods. These include, but are not limited to: (1) ligating a small RNA or DNA oligonucleotide produced synthetically and containing one or more biotins to the 3' terminus with T4 RNA ligase (2) addition of an RNA tail to the 3' terminus with E. coli poly A polymerase using biotinylated ribonucleoside triphosphates (3) periodate oxidation of the 3' terminal residue, followed by coupling of the dialdehyde product to a biotinylated molecule bearing a primary amine followed by reduction, and (4) hybridization of a biotinylated complementary RNA to a region distal (e.g.-3' to) the target-binding region of the midivariant probe.

Turning now to methods of the present invention which relate to diagnostics, the methods of the present invention feature each of the composition herein described. This discussion will focus on selected compositions by way of example, without limitation. One embodiment of the present invention includes a method for detecting the presence of a target nucleic acid in a sample comprising the steps of contacting a sample with a first nucleic acid which nucleic acid has a first section and a second section. The first section is capable of autocatalytic replication under reaction conditions. The first section has a 3' end and a 5' end. The second section is positioned at one of the ends of the first section and is capable of assuming a bound position in the presence of binding conditions with target. The method further includes the step of imposing binding conditions on the sample to allow the first nucleic acid to form a target-first nucleic acid complex. Unbound first nucleic acid is separated from the sample. The imposition of reaction conditions for autocatalytic replication on the sample allows the sample to be monitored for the presence of the autocatalytic reaction product which will be formed in the presence of the first nucleic acid, which reaction product is indicative of the presence of the target.

A further embodiment of the present invention includes a first section which has sequences which are substantially identical to MDV-1 and is capable of autocatalytic replication in the presence of the enzyme Q-beta replicase. Preferably, in imposing reaction conditions, which reaction conditions Include contacting the sample with the enzyme Q-beta replicase, an enzyme is used which has no endogenous activity. Surprisingly and unexpectedly, when such nucleic acid compositions with first sections having sequences substantially identical to MDV-1, and second sections capable of binding to target, are used with the enzyme Q-beta replicase, it is possible to discern the presence of target from what had been previously characterized as "unprimed" activity.

A further embodiment includes a method for detecting the presence of target nucleic acid in a sample comprising the step of contacting the sample with a first nucleic acid which nucleic acid has a first section, and second section and is associated with an inhibitory element. Each section has a 5' end and a 3' end. The first section is capable of active autocatalytic replication under reaction conditions when the first section is separated from the inhibitory element and is inactive when integral and associated with the inhibitory element. The second section is positioned at one of the ends of the first section and is capable of cleavage upon interaction with release means, to separate the first section from the inhibitory element. At least one section or the inhibitory element of the first nucleic acid is capable of assuming a bound position to target in the presence of binding conditions. Imposition of binding conditions on the sample in the first nucleic acid allows the formation of a target first nucleic acid complex in the presence of target. The sample is contacted with release means to separate the first section from the inhibitory element. Imposition of autocatalytic replication reaction conditions on the sample, allows the formation of an autocatalytic reaction product in the presence of the first nucleic acid. The sample is monitored for the presence of the autocatalytic reaction product, which autocatalytic reaction product is indicative of presence of target.

The present method is compatible with additional steps, such as separating unbound first nucleic acid from the sample. However, in situations where the distinction between active and inactive is large, such separation steps may not be necessary.

The release means may take many forms. In one embodiment, the release means is an enzyme or nuclease. By way of example, the enzyme RNase H or a ribozyme.

One embodiment of the present Invention features a ribozyme formed by the first nucleic acid and the target. The method incorporates additional "smartness" due to the need for specific target sequences which do not allow a ribozyme to form unless the first nucleic acid is bound to target. One embodiment features a ribozyme which requires target sequences to form the ribozyme.

In a further embodiment, the method includes the formation of a ribozyme comprising a first nucleic acid and a second nucleic acid, both of which can be made to interact with target in order to form stable ribozyme structures.

In one structure resembling a "hammerhead," the target contributes the sequences 5'-MGAAAK-3' (SEQ ID NO:2), a first nucleic acid or second nucleic acid has a section or an area which contributes the sequences 5'-J'CUGANGAM'-3' (SEQ ID NO:3), and first nucleic acid has a section which contributes the sequences 5'-K'UWJ-3' (SEQ ID NO:4). As used herein, N is one of the four nucleotides U, G, A and C. The letter W represents C or A. The letters J, J', K, K', M and M' each represent four or more nucleotides. The nucleotides of J and J' are complementary, as are the nucleotides of K and K' and the nucleotides of M and M'.

In one structure resembling a "hairpin," the first nucleic acid has a section having the sequences 5'-FNGUCQ-3' (SEQ ID NO:5) and a second nucleic acid has a second area having the sequences 5'-Q'AGAAF'ACCAGAGAAACAC- ACGUUGUGGUAUAUUACCUGGUA-3' (SEQ ID NO:6). The letters Q and Q' each represent four or more nucleotides. The letters F and F' each represent four nucleotides. The nucleotides of Q and Q' as well as F and F' are complementary.

Inhibitory elements for inactivating the autocatalytic replicatable section of the first nucleic acid may take different forms. One embodiment of the present invention features a first nucleic acid further comprising inhibitory sequences. The inhibitory sequences are capable of interacting with the first section rendering the first section inactive. In the situation where the first section includes sequences substantially identical to the MDV-1 molecule, the inhibitory sequences interact with the sequences in approximately the 81 to 126 nucleotide region. A preferred embodiment includes a Inhibitory sequences comprising the sequences 5'UUYRC3' (SEQ ID NO:1), wherein Y represents any pyrimidine nucleotide and R is any purine nucleotide. One embodiment features inhibitory sequences where Y is U and R is A.

Additional embodiments of the present invention relate to compositions of matter which are useful as ribozymes. One embodiment of the present invention features a first nucleic acid and a second nucleic acid in which the first nucleic acid has a first section and a second section. Each section having a 5' end and a 3' end. The first section has less than all the sequences performing a ribozyme and the second section is capable of assuming a bound position with a target and is positioned at one of the ends of the first section. The second nucleic acid has a first area and a second area, each area having a 5' end and a 3' end. The first area has sequences which complete the formation of a ribozyme when the first area is held in a cooperating relationship with the first section of the first nucleic acid. The second area is capable of assuming a bound position to target in which the first area is held in cooperating relationship.

In one embodiment of the present invention, the ribozyme resembles a "hammerhead." In one "hammerhead" configuration, the target contributes the sequences 5'-MGAAAK-3' (SEQ ID NO:2) for the completion of the ribozyme. The first section of the first nucleic acid includes the sequences 5'-J'CUGANGAM'-3' (SEQ ID NO:3) wherein the letter N is used to represent a nucleotide selected from the group of nucleotides consisting of A, G, U or C. The first area of the second nucleic acid contributes sequences 5'-K'UWJ-3' (SEQ ID NO:4). The letter W represents C or A. The letters J, J', K, K', M, and M' each represent four or more nucleotides. The nucleotides of J and J' are complementary, as are the nucleotides of K and K', and the nucleotides of M and M'.

In a further embodiment the ribozyme resembles a "hairpin." In the "hairpin" configuration, the first area comprises sequences 5'-Q'AGAAF'ACCAGAGAAACACACGUUG-UGGUAUAUUACCUGGUA-3' (SEQ ID NO:6), and, the first section of the first nucleic acid comprises the sequences 5'-FNGUCQ-3' (SEQ ID NO:5). The letters Q and Q' each represent four or more nucleotides. The letters F and F' each represent four or more nucleotides. The nucleotides of Q and Q' are complementary as are the nucleotides of F and F'.

Further embodiments of the present invention feature methods of making ribozymes. In one embodiment, the method includes binding a first and second nucleic acid to a target in cooperating relationship. The first nucleic acid has less than all sequences for ribozyme activity. The second nucleic acid has less than all sequences necessary for all ribozyme activity and in a bound position, form a ribozyme.

In order to facilitate an understanding of the invention, the discussion with respect to ribozymes and methods has focused on particular sequences and structures which are known in the art to have nucleotides which can be substituted or modified. The present invention encompasses all such modifications and substitutions.

In order to facilitate an understanding of the invention, the discussion with respect to ribozyme compositions and methods of making ribozymes has focused on nucleic acid probes. However, sections and areas of the first and second nucleic acid which bind to a target can be substituted with any ligand which binds to a target to position sections and areas which form a catalytic sequence group. Embodiments of the present invention featuring the formation of ribozymes encompass the use of probes in a broad sense including immunodiagnostic agents, such as antibodies and antigens, and other biological binding pairs such as, drugs and drug receptor sites, enzymes and enzyme substrates.

Other features and advantages in the present invention will be apparent from the following description, examples and illustrations, which by way of example, demonstrate preferred embodiments of the present invention and the principles thereof and what is now considered to be the best mode to apply these principles. Those skilled in the art will readily recognize that the following drawings and detailed examples are capable of modification and alteration and the present invention should not be limited to the precise details set forth.

BRIEF DESCRIPTION OF THE DRAWINGS

FIG. 1, consisting of FIG. 1A and FIG. 1B, illustrates a method of determining the presence of a target molecule which target molecule is capable of contributing sequences to form a ribozyme in a "hammerhead" configuration.

FIG. 2 generally depicts an alternative "hammerhead" ribozyme configuration.

FIG. 3 generally illustrates a first and second nucleic acid bound to target forming a ribozyme in a "hairpin" configuration.

FIG. 4 illustrates a structure of a ribozyme with an autocatalytic replicating section associated with a support, in the presence of target.

FIG. 5 generally Illustrates a construction scheme for a cDNA clone for use in generating first and second nucleic acids herein described.

FIG. 6, which consists of FIGS. of 6A and 6B, generally describes the use of a cDNA clone produced in FIG. 4 in the construction of a vector to produce the first nucleic acid and second nucleic acid of embodiments of the present invention.

DETAILED DESCRIPTION OF THE DRAWINGS AND EXAMPLES

To facilitate discussion of the present invention, reference will be made to the figures which describe methods and compositions for the detection of target. However, those skilled in the art will readily recognize that the methods and compositions of the present invention have value and application in therapeutics to deliver molecules to sites for activation.

Turning now to FIG. 1, which consists of FIGS. 1A and 1B, a method of detecting the presence of a target molecule is generally depicted.

As illustrated, the target molecule is a nucleic acid generally designated by the number 11. The target molecule is associated with a capture bead 13 by means of a capture ligand 15 which is hybridized to a capture nucleic acid, generally described by numeral 21. The capture nucleic acid 21 has a capture antiligand section generally described by the numeral 23 and a probe section 25 capable of hybridizing to the target 11. The capture nucleic acid is illustrated in a hybridized position to the target 11.

The target 11 has a first segment 26 and a second segment 27 and a third section 29. The first segment 26 and third segment 29 define binding sites. The second segment 27 has sequences which participate in the formation of a ribozyme.

Figure 2:
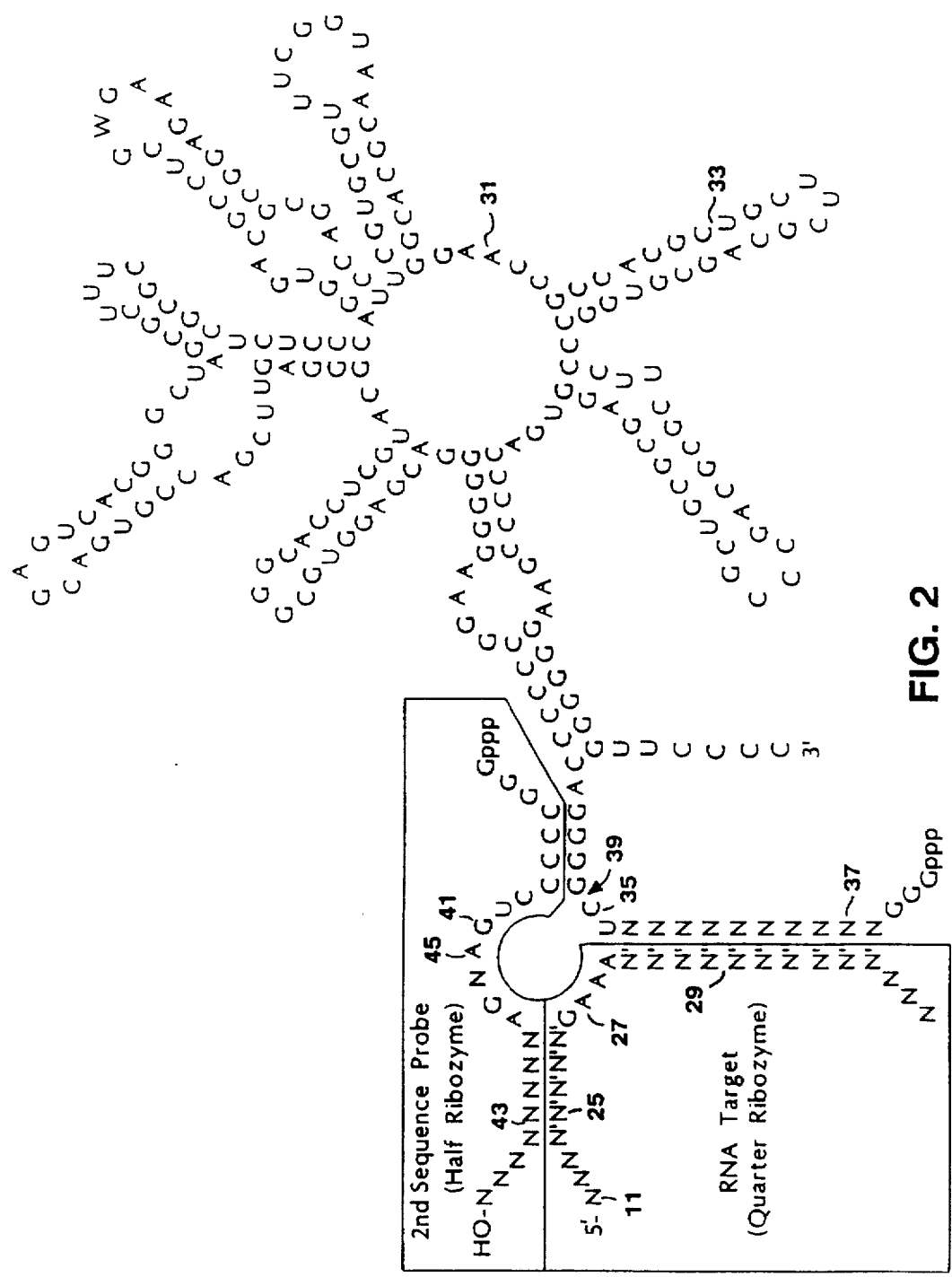
Figure 3:
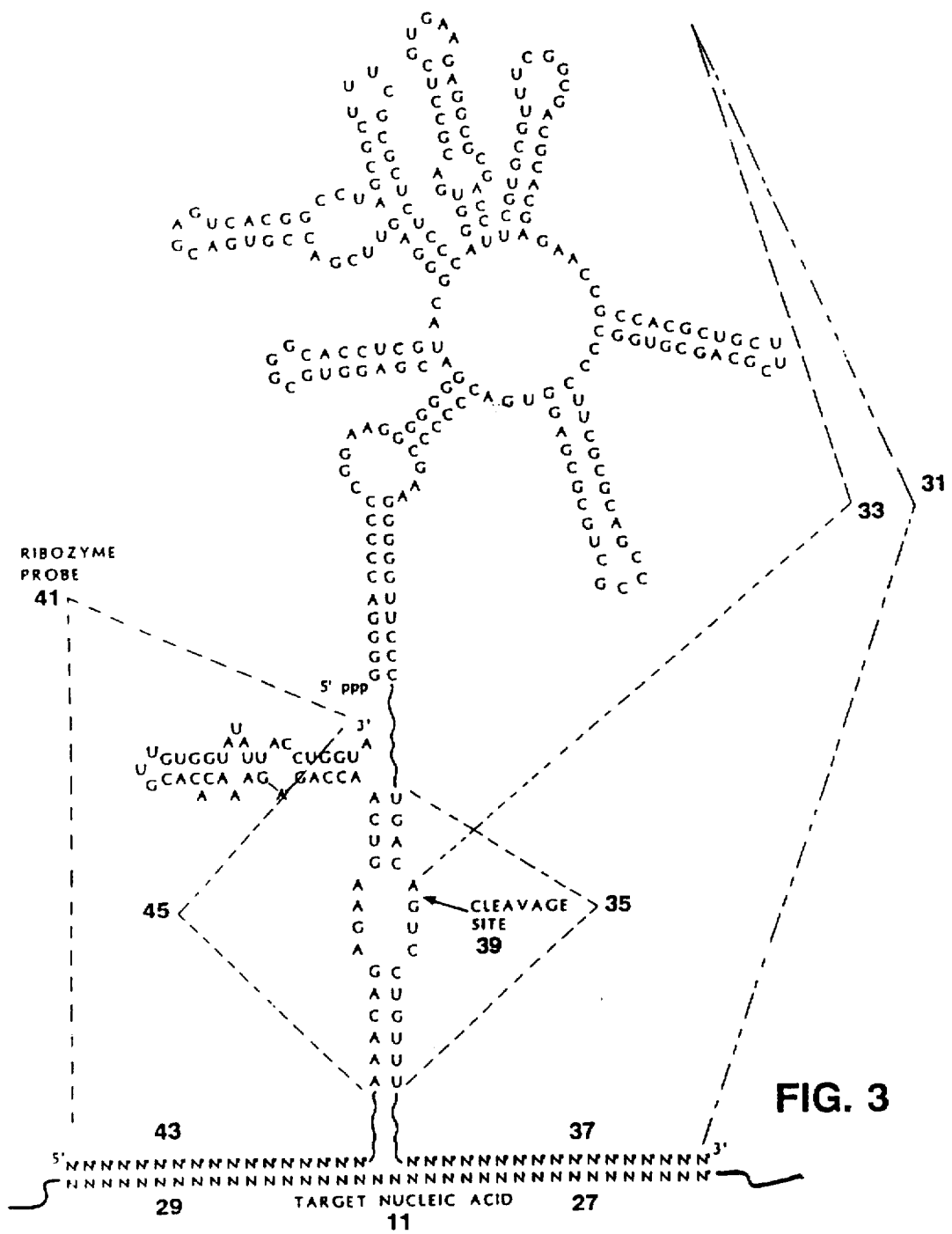
Figure 4:
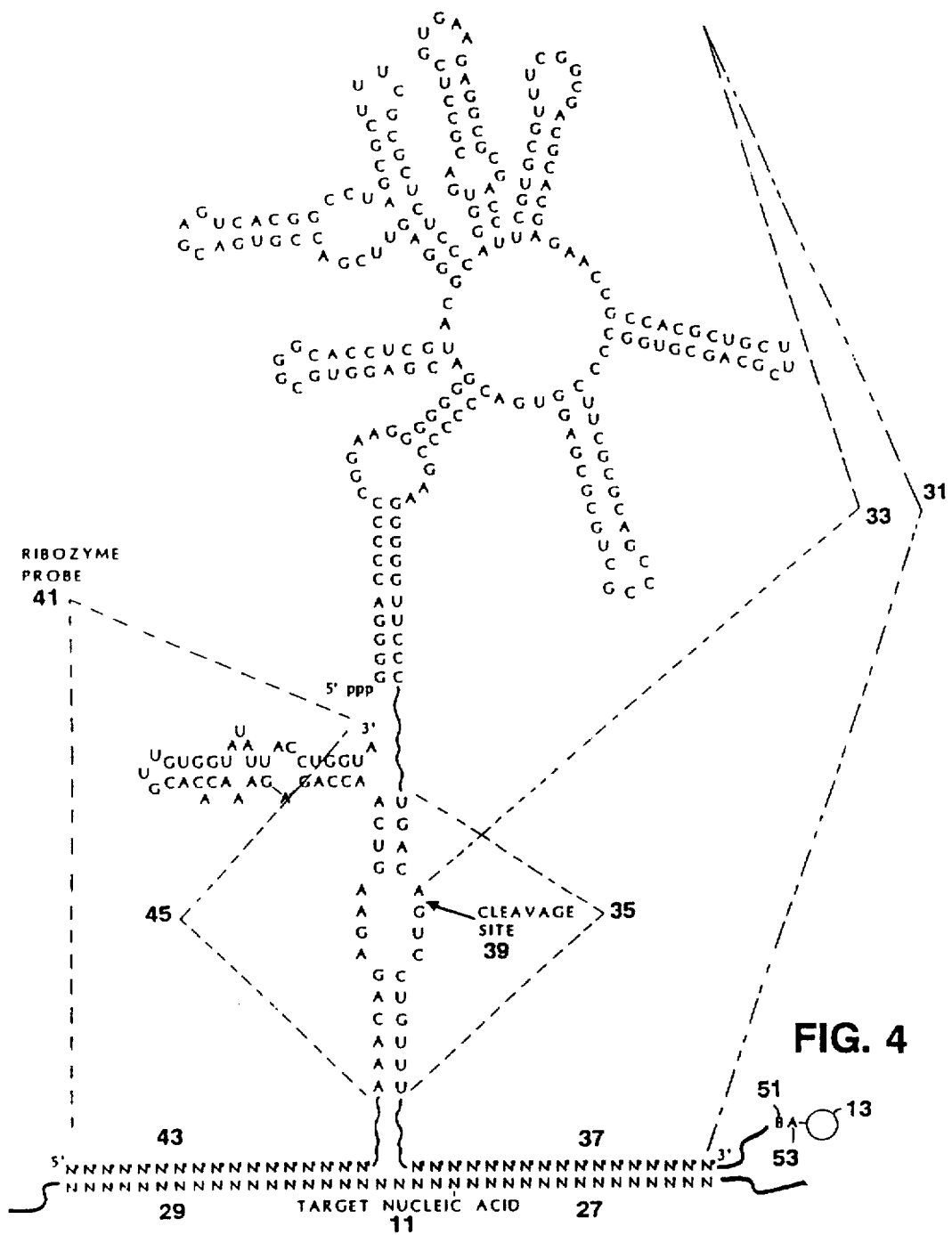

A first nucleic acid 31 is illustrated bound to the target 11. The first nucleic acid 31 has a first section 33, second section 35, a third section 37 (as can be seen in FIGS. 2, 3, and 4) and a fourth section 41. The first section 33 is capable of autocatalytic replication. As illustrated, the sequences of the first section 33 includes sequences that are substantially identical to the sequences of MDV-1. The second section 35 has sequences which are able to participate in the formation of a ribozyme. The third section 37 is capable of binding to the target at the target segment 27. The fourth section 41 includes at least four base sequences 43 capable of binding the target at target third segment 29, and contributes sequences to the formation of the ribozyme. The sequences of the fourth section 41 which participate in ribozyme formation are generally designated by the numeral 45 and those sequences capable of binding target are designated 43. Upon imposition of ribozyme reaction conditions in the presence and target, the first nucleic acid 31 is capable of cleavage in second section 35 (see FIGS. 2 and 3) at the position designated as 39.

Upon imposition of ribozyme reaction conditions, first nucleic acid 31 is cleaved at the cleavage site 39 allowing the first section 33 to become separate from the third section 37. Separation from the third section 37 allows the first section 33 to become activated as generally depicted in FIG. 1B.

Thus, in FIG. 1B, the first section 33 is shown as a distinct part from the rest of the first nucleic acid 31. The few remaining nucleotides of the fourth section 41 which are capable of binding to the second nucleic acid at 29, are unable to form a stable hybrid under the conditions present in the sample. The first section 33 becomes disassociated from the target-probe complex and receptive to autocatalytic replication reaction conditions.

Upon imposition of autocatalytic reaction conditions, the first section 33 is replicated on an exponential basis initially. The fourth section 41 need not, and normally is not, replicated. Upon saturation of the enzyme Q-beta replicase with the first section 33 and its copies, the first section 33 and its copies are replicated in a linear fashion. In a diagnostic assay, the sample is monitored for the presence of the autocatalytic reaction product which product is indicative of the presence of target 11. Additionally, if one monitors the concentration of the autocatalytic reaction product, the concentration of target 11 can be calculated on the basis of the amount of autocatalytic reaction product produced in time.

FIG. 2 describes an alternative "hammerhead" ribozyme structure formed by target 11, and a first nucleic acid 31 and a second nucleic acid 41. The ribozyme structure depicted in FIG. 2 has a cleavage site 39 is positioned towards the 5' end of the first nucleic acid 31.

The target 11 includes a first segment 25, second segment 27 and a third segment 29. A first nucleic acid 31 includes a first section 33, a second section 35 and a third section 37. The first section includes base sequences which are substantially identical to MDV-1 and are capable of autocatalytic replication when removed from the third section 37. The second section 35 is capable of contributing sequences which form a ribozyme. The third section 37 is capable of binding to the target 11 at the third segment 29.

A second nucleic acid 41 includes a first area 43 and a second area 45. The first area 43 is capable of binding to the target 11 at first segment 25. The second area 45 of the second nucleic acid 41 is capable of contributing sequences to form a ribozyme.

As illustrated, the target 11 itself contributes sequences to the ribozyme, which sequences include the sequences 5'-GAAA-3' (SEQ ID NO:7). Individuals skilled in the art will recognize that the designation of target 11 and second nucleic acid 41 is somewhat arbitrary, depending on the molecule of interest and what sequences are available in such molecule. It is much more probable that a particular molecule of interest will have the sequences 5'-GAAA-3' (SEQ ID NO:7), than the sequences 5'-CUGANGA-3' (SEQ ID NO:8). In a bound position to the target 11 the first nucleic acid 31 and the second nucleic acid 41 form a ribozyme which upon imposition of ribozyme reaction conditions cause cleavage at position 39, releasing the first section 33 from the third section 37. The first section 33, removed from the third section 37 is capable of autocatalytic replication upon imposition of autocatalytic replication reaction conditions.

Turning now to FIG. 3, a target is illustrated generally depicted as 11 in which a first nucleic acid 31 and a second nucleic acid 41 are bound. The first nucleic acid 31 and the second nucleic acid 41 create a "hairpin" ribozyme structure. The target 11 includes a first segment 27 and a second segment 29 each having a 5' end and a 3' end. The first nucleic acid 31 includes a first section 33, a second section 35 and a third section 37. The first section 33 is capable of autocatalytic replication in the presence of autocatalytic reaction conditions and upon separation from the third section. The second area 35 is capable of contributing sequences to a ribozyme structure. The third section 37 is capable of binding to the first segment 27 of the target 11.

The second nucleic acid 41 includes a first area 43 and a second area 45, each area having a 5' end and a 3' end.

To facilitate synthesis and cloning manufacturing, each area of the second nucleic acid 41 is linked by a conventional phosphodiester bridge 5' to 3' or 3' to 5'. The first area 43 is capable of assuming a bound position to the second segment 29 of the target 11. The second area 45 of the second nucleic acid 41 is capable of forming a "hairpin" ribozyme with the second section 35 of the first nucleic acid 31. The second area 45 of the second nucleic acid 41 and the second section 35 of the first nucleic acid 31 define a ribozyme having a cleavage site 39 on the first nucleic acid 31.

Upon imposition of ribozyme reaction conditions, the ribozyme formed by the first nucleic acid 31 and the second nucleic acid 41 causes cleavage at the cleavage site 39 of the first nucleic acid 31 releasing the first section 33 of the first nucleic acid 31 from the third section 37. Separation from the third section 37 allows the first section 33 to become active and autocatalytically replicated upon imposition of autocatalytic replication reaction conditions. As illustrated, first section 33 includes sequences which are substantially identical to MDV-1. First section 33 is replicatable in the presence of the enzyme Q-beta replicase and necessary cofactors.

FIG. 4 illustrates compositions similar to that illustrated in FIG. 3. A target is illustrated generally depicted as 11 in which a first nucleic acid 31 and a second nucleic acid 41 are bound. The first nucleic acid 31 and the second nucleic acid 41 create a "hairpin" ribozyme structure. The target 11 includes a first segment 27 and a second segment 29 each having a 5' end and a 3' end. The first nucleic acid 31 has a first section 33, a second section 35 and a third section 37. The first section 33 is capable of autocatalytic replication in the presence of autocatalytic reaction conditions and upon separation from the third section. The second area 35 capable of contributing sequences to a ribozyme structure. The third section 37 is capable of binding to the first segment 27 of the target 11, and Is associated with support means 51. Support means 51 is biotin which is capable of binding to avidin 53 bound to support 13.

The second nucleic acid 41 includes a first area 43 and a second area 5' each area having a 5' end and a 3' end.

To facilitate synthesis and cloning manufacturing, each area of the second nucleic acid 41 is linked by a conventional phosphodiester bridge 5' to 3' or 3' to 5'. The first area 43 is capable of assuming a bound position to the second segment 29 of the target 11. The second area 45 of the second nucleic acid 41 is capable of forming a "hairpin" ribozyme with the second section 35 of the first nucleic acid 31. The second area 45 of the second nucleic acid 41 and the second section 35 of the first nucleic acid 31 define a ribozyme having a cleavage site 39 on the first nucleic acid 31.

After a complex of the target 11 with the first nucleic acid 31 and second nucleic acid 41 is formed, the first nucleic acid 31 is captured on support 13 through the biotin 51 and avidin 53. The support 13 is separated from the remaining solutions, which may include first nucleic acid 31 unbound to target 11, and first sections 33 which have dissociated from the first nucleic acid 31 through an event not mediated by target 11, to reduce background.

Upon imposition of ribozyme reaction conditions, the ribozyme formed by the first nucleic acid 31 and the second nucleic acid 41 causes cleavage at the cleavage site 39 of the first nucleic acid 31 releasing the first section 33 of the first nucleic acid 31 from the third section 37. Separation from the third section 37 allows the first section 33 to become active and autocatalytically replicated upon imposition autocatalytic replication reaction conditions. As illustrated, first section 33 includes sequences which are substantially identical to MDV-1. First section 33 is replicatable in the presence of the enzyme Q-beta replicase and necessary cofactors.

Figure 5:
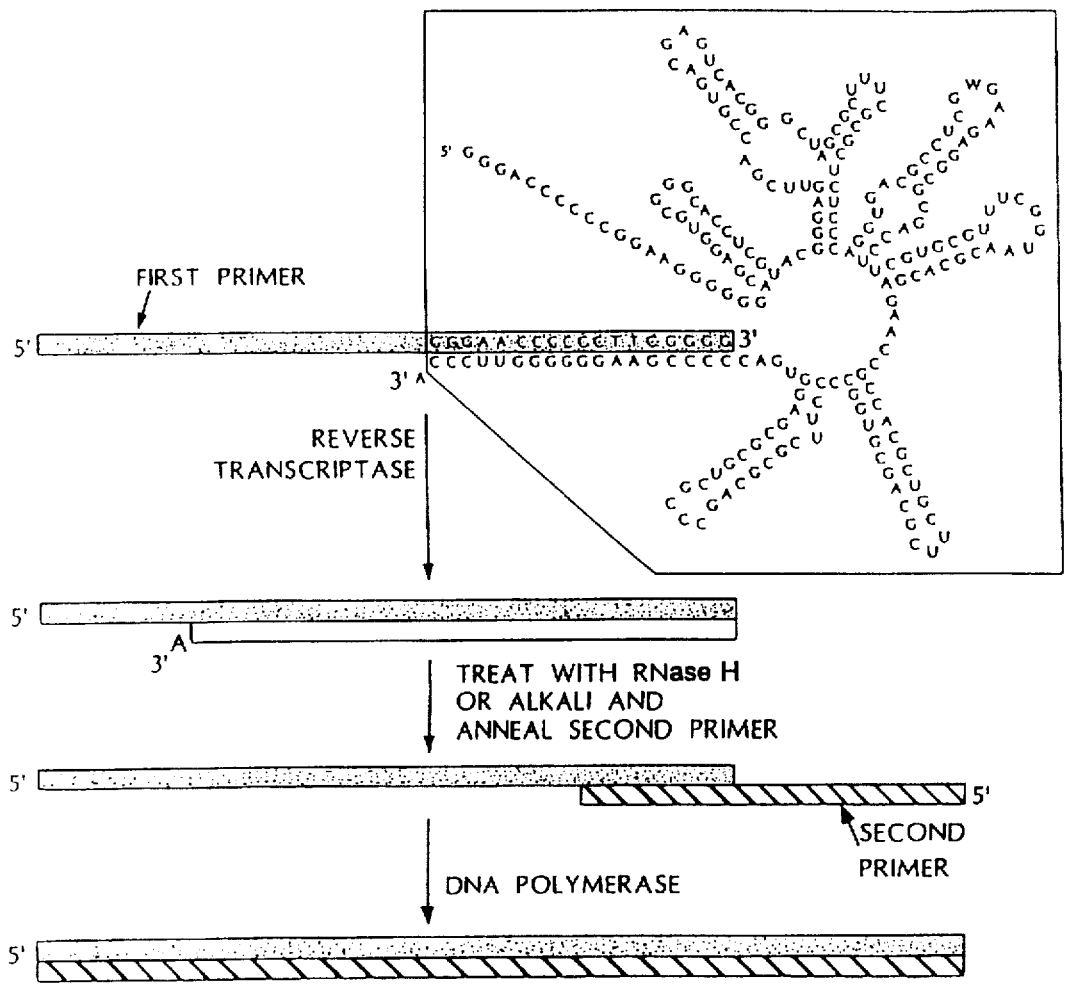
Figure 6A:
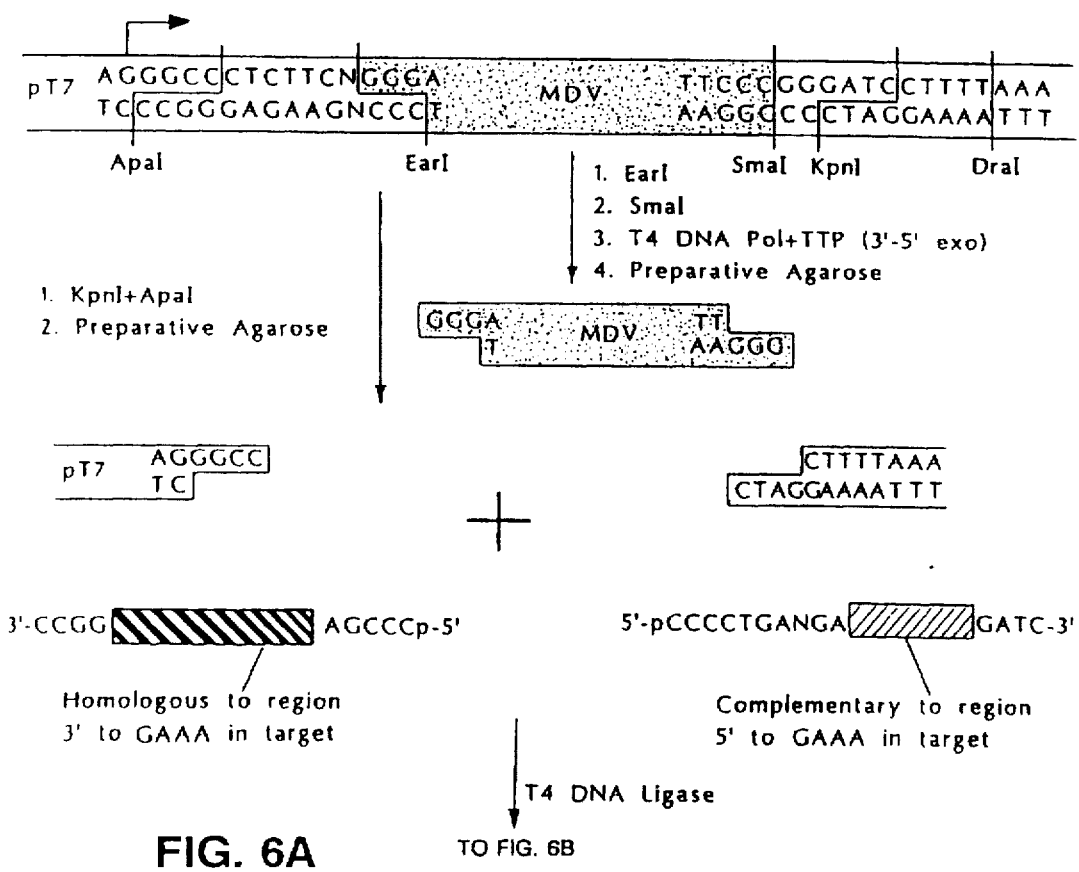
Figure 6B:
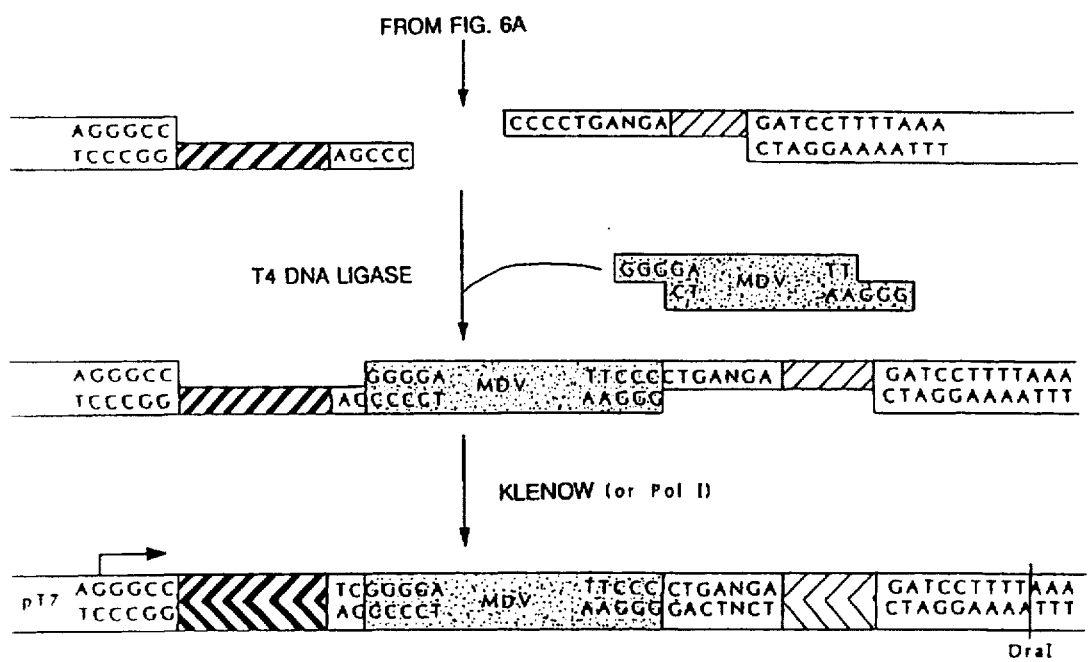

FIGS. 5, 6A and 6B will be further described in relation to Example 1 which describes the production of ribozyme: Q-beta template RNA probe chimeras.

EXAMPLES

Example 1

Production of a Ribozyme:Qβ template RNA probe Chimera.

The RNA construct illustrated in FIG. 1 is produced by the following method. Two synthetic oligonucleotide primers are produced by methods familiar to those skilled in the art. The first contains one strand of a number of recognition sequences of the restriction endonucleases used for subsequent constructions (see FIG. 6A), joined to a portion complementary to the sequence proximal to but not containing the ultimate 3' nucleotide, A, of the plus strand of midivariant RNA, a template for the enzyme Qβ replicase. As will be understood by those skilled in the art, the exact length of a sequence complementary to this region of the RNA must be of sufficient length to form an intermolecular hybrid and displace the intramolecular base pairing present in the midivariant RNA in this region. The second oligonucleotide contains, in order from its 5' to 3' end, the sequence comprising one strand of the promoter for a DNA-dependent RNA polymerase read in the same sense as the direction or transcription. In this case, said promoter is that for the RNA polymerase encoded by the bacteriophage T7, a highly efficient enzyme, although as will be understood by those skilled in the art, promoters for other RNA polymerases can be used as well. This sequence element is followed, in the 3' direction by a cleavage site for a restriction endonuclease which produces a staggered break in double-stranded DNA, and which leaves a protruding single-stranded 3' terminal extension. In this example, this enzyme is Apa I, and its sequence is made to partially overlap the promoter for T7 RNA polymerase. This site is followed by a recognition sequence for a restriction endonuclease which may be any member of a class of enzymes which recognize a sequence and cleave the DNA in a region 3' to that sequence element, and which leave a staggered cleavage and a protruding single-stranded 5' terminal extension. This recognition sequence is placed in such a manner as to direct the cleavage of the final DNA vector construct in one strand immediately prior to the sequence encoding the midivariant RNA. In this example (see FIG. 6A), this is the site for the restriction endonuclease Ear I which recognizes the sequence CTCTTCN, where N is any nucleotide, and cleaves the DNA in the same strand after the nucleotide N, and three nucleotides further in the complementary strand. Finally, this sequence is followed by another sequence homologous to the sequence proximal to and including the 5' terminus of midivariant RNA (MDV-1 RNA) which is of sufficient length to anneal and prime the synthesis of a second strand product as described below, except that deoxyribonucleotides replace the ribonucleotides found in MDV-1. The first oligonucleotide is used as a primer for the synthesis of a cDNA of midivariant RNA as shown in FIG. 5. MDV-1 is obtained from a Qβ replicase reaction initiated without exogenous template RNA. This will generate abundant levels of MDV-1 RNA because all preparations of Qβ replicase holoenzyme prepared by any of a number of methods typically are contaminated by low levels of this RNA. One picomole each of the first oligonucleotide described above and MDV-1 are mixed and annealed by heating and allowing the mixture to cool slowly. This primer-template combination is used to initiate a reverse transcriptase reaction in a manner such as those described by Maniatis et al., A Cloning Manual. After completion of the first strand synthesis, the midivariant RNA is destroyed by mild alkali treatment or alternately, RNase H. The second complementary strand is generated by annealing the product of this reaction with the second oligonucleotide described above and extending with a DNA-dependent DNA polymerase. This product can then be cloned into a selectable, replicatable DNA vector in a manner such as that described by Maniatis et al. Potential clones are screened for the presence of each of the restriction endonuclease sites included in the oligonucleotides by conventional methods.

After propagation in and purification from bacteria, the cloned cDNA is cleaved with the restriction endonuclease Apa I and Kpn I. The smaller fragment is purified electrophoretically, and cleaved with the restriction endonuclease Hinf I. This enzyme cleaves the cDNA at the site corresponding to position 65 in MDV-1. In the naturally occurring population of MDV-1 RNAs, however, this site occurs in only a fraction of the molecules. Thus, a number of clones must be screened for those which possess the appropriate sequence. Once thusly obtained, the Hinf subfragments are ligated to the oligonucleotide 5'-pGA$_{10}$-3' annealed to the oligonucleotide 5'pCT$_{10}$-3'. This ligation mixture is digested with Apa I and Kpn I. The resultant mixture is ligated into the large fragment resulting from digestion of the vector produced above with Apa I and Kpn I. This will generate a clone in which the DNA sequence encoding the midivariant is interrupted by tract of A residues. Any of a number of sequences may be substituted for the A$_{10}$ tract utilized in this example. However, A$_{10}$ is known to be maintained during replication of midivariant RNA, as shown by Miele, et al. (J. Mol. Biol. (1983 281–295).

After propagation in and purification from bacteria, the cloned DNA from the construction above is cleaved in two separate reactions (see FIG. 6A). In the first of these, the segment bearing the complete midivariant RNA cDNA is excised with the enzymes Ear I and Sma I. This digest is treated with T4 DNA polymerase in the presence of thymidine triphosphate to remove three nucleotides from the 3' end of the strand bearing the sequence in the same sense as the MDV-1 plus strand (e.g. the strand shown in FIG. 1, its complement is the minus strand, also a replicatable RNA template). The resulting modified fragment is purified by electrophoresis through polyacrylamide gels. The second restriction digest is with the enzymes Apa I and Kpn I. The larger of the two fragments is purified by agarose gel electrophoresis.

Two oligonucleotides are synthesized. The first of these advantageously contains the sequence 5'-CCCCTGANGA-3' (SEQ ID NO:10) followed by at least four nucleotides complementary to the sequence in the target RNA 5' to the 5'-GAAA-3' (SEQ ID NO:7) element and terminating in the sequence 5'-GATC-3' (SEQ ID NO:11). The second oligonucleotide ideally contains the sequence 5'-CCCGA-3' (SEQ ID NO:12) followed by at least 4 nucleotides of the sequence 3' to the 5'-GAAA-3' (SEQ ID NO:7) element in the target, except that deoxyribonucleotides replace the ribonucleotides of the target. This element is advantageously followed Immediately by the element 5'-GGGG-3' (SEQ ID NO:13). Each of the oligonucleotides is phosphorylated on its 5' terminus by T4 polynucleotide kinase.

Both of the oligonucleotides are ligated to the large fragment produced by the Kpn I, Apa I digest of vector DNA in a reaction containing T4 DNA ligase and ATP such as those described by Maniatis et al. (ibid). The ligation product (see FIG. 4B) is purified away from unligated oligonucleotides by gel filtration. The ligation product is then ligated to the small Ear I, Sma I fragment bearing the modified terminus. The resulting "gapped" molecule is rendered fully double-stranded by treatment with a DNA-dependent, DNA polymerase. This product may be advantageously introduced into and propagated in bacteria.

As will be obvious to those skilled in the art, this series of manipulations will generate DNA clones in which the MDV cDNA portion is inserted in both its normal and inverted orientation relative to the direction of transcription by T7 RNA polymerase. The clones containing the MDV cDNA in plus strand orientation (oriented such that transcription produces an RNA containing the plus strand of MDV-1) are determined by screening for restriction endonuclease fragments of the appropriate size which are known to cleave within the MDV-1 cDNA sequence.

The DNA prepared from a clone with the MDV-1 in the plus strand orientation is cleaved at a restriction site distal to the second probe element relative to the promoter. In this example, this is the restriction endonuclease Dra I. This digested DNA is advantageously transcribed by T7 RNA polymerase in vitro under conditions such as those described by Milligan et al. (Nucl. Acid. Res. (1987)15:8783–8798) to generate the RNA probe.

Example 2
Assembly of a Bimolecular Ribozyme Probe Set

The cDNA clone as described in Example 1 is cleaved with the enzymes Apa I and Ear I, and the large fragment is ideally purified away from the small fragment described above. An oligonucleotide having the sequence 5'-CCCGA-3' (SEQ ID NO:12) followed by 4–50 nucleotides identical to the sequence immediately 3' to a 5'-GAAA-3' (SEQ ID NO:7) element in the target, in turn followed by the sequence 5'-GGCC-3' (SEQ ID NO:14) is synthesized by any of a number of methods familiar to those skilled in the art. This oligonucleotide is annealed and ligated to the large restriction fragment, and the resulting single stranded "gap" region rendered double-stranded by the action of a DNA-dependent DNA polymerase. This DNA is introduced into and propagated within bacteria. After purification from bacteria, it may be cleaved with the restriction endonuclease Sma I, and then used as a template in an in vitro transcription reaction utilizing bacteriophage T7 RNA polymerase.

The second sequence probe may be generated by constructing a synthetic DNA template for T7 RNA polymerase as described by Milligan et al. (Nucl. Acid. Res. (1987) 15:8783–8798), one strand of this template starting at its 5' end with at least 4 nucleotides of the sequence from the region 5' to the 5'-GAAA-3' (SEQ ID NO:7) element in the target except that deoxyribonucleotides replace the ribonucleotides found in the target, followed by the sequence 5'-TCNTCAGGGGGCCCTATAGTGAGTCGTATTA-3' (SEQ ID NO:15) where N indicates any nucleotide having the sequence 5'-TAATACGACTCACTATAG-3' (SEQ ID NO:16). These two oligonucleotides preferably are mixed and transcribed in vitro as described by Milligan et al. (ibid). The product may be readily purified by any of a number of methods familiar to those acquainted with the art.

Example 3
Replication of modified MDV-1 RNAs bearing 3'-terminal extensions

A cDNA clone of MDV-1 similar to that described in Example 1, was obtained from F. R. Kramer of Public Health Research Institute, New York City, and contained a promoter for T7 RNA polymerase, and a modified MDV-1 cDNA sequence in which the sequence element 5'-CTCTAGATCTCGAGACTAACATAGGTCTTAACTT-GACTAACATCGAGGCCTGCTAGAG-3' (SEQ ID NO:17) replaced the 3-nucleotide segment encoding nucleotides 64–66 in the naturally-occurring MDV-1 RNA, followed by the sequence 5'GGGAATTC-3' (SEQ ID NO:18). This entire sequence was cloned between the Hind III site and the EcoRI site of pSP64 (Melton, et al., Nucl. Acid. Res., Vol. 12, 7035–7056). This plasmid was cleaved separately with the restriction endonucleases Sma I, Eco RI, Alu I, and Pvu II, and each of the cleaved preparations transcribed In vitro by T7 RNA polymerase under conditions described by Milligan et al. The RNAs produced in these reactions were purified by denaturing polyacrylamide gel electrophoresis. This procedure resulted in the generation of modified MDV-1 molecules bearing either no extension beyond the 3' terminus found in the naturally-occurring MDV-1 RNA, a 7-Nucleotide 3' extension, a 24-nucleotide 3' extension, or a 183-nucleotide 3' extension.

The purified RNAs were serially diluted and $10^4$ molecules used to prime a Qβ replicase reactions as described by Chu et al. (Nucl. Acid. Res. (1986) 14:5591–603), except that the Qβ replicase was that purified from the expression clone of the replicase described by Biebricher et al. (Nature (1986) 321:89–91) and physically obtained from C. Biebricher (Max Plank Institute). After 30 minutes, two microliters of each reaction was mixed with 18 microliters 95% formamide, heated to 100° C. for 5 minutes, and resolved by electrophoresis on an 8% polyacrylamide gel containing 8.3M urea. The replicated recombinant RNAs were distinguished from the MDV-1 RNA which contaminates the enzyme preparation and is also replicated, by their larger size resulting from the larger sequence replacing nucleotides 64–66, which in turn results in a lower electrophoretic mobility. The recombinant RNA product represented approximately 50%, 86%, 72%, and 15% of the total RNA when the reaction was initiated with the modified MDV-1 RNAs bearing either no 3' extension, the 7-nucleotide extension, the 24-nucleotide extension, or the 183-nucleotide extension, respectively. The recombinant RNAs produced in each case were the same size as the recombinant RNA which lacked a 3' terminal extension, indicating that the 3' extension itself is not replicated with the rest of the molecule. This experiment has been repeated with a number of 3' terminal extensions of different sequence with comparable results.

Example 4

An assay for target nucleic acid utilizing a ribozyme probe.

Two deoxyribo-oligonucleotides are synthesized with the following sequence: 5'-CCCGAGGATCACCAGCAATA-TTCCAAAGTAGCATGACAAAAATCTTGGCC-3' (SEQ ID NO:19), and 5'-CCCCCTTGACGACATCCCGATC-3' (SEQ ID NO:20). These are cloned into the cDNA vector described in Example 1, and the purified cloned DNA transcribed with T7 RNA polymerase after cleavage with the restriction endonuclease Dra I. The RNA product of the correct size is purified by denaturing polyacrylamide gel electrophoresis.

Figure 1B:
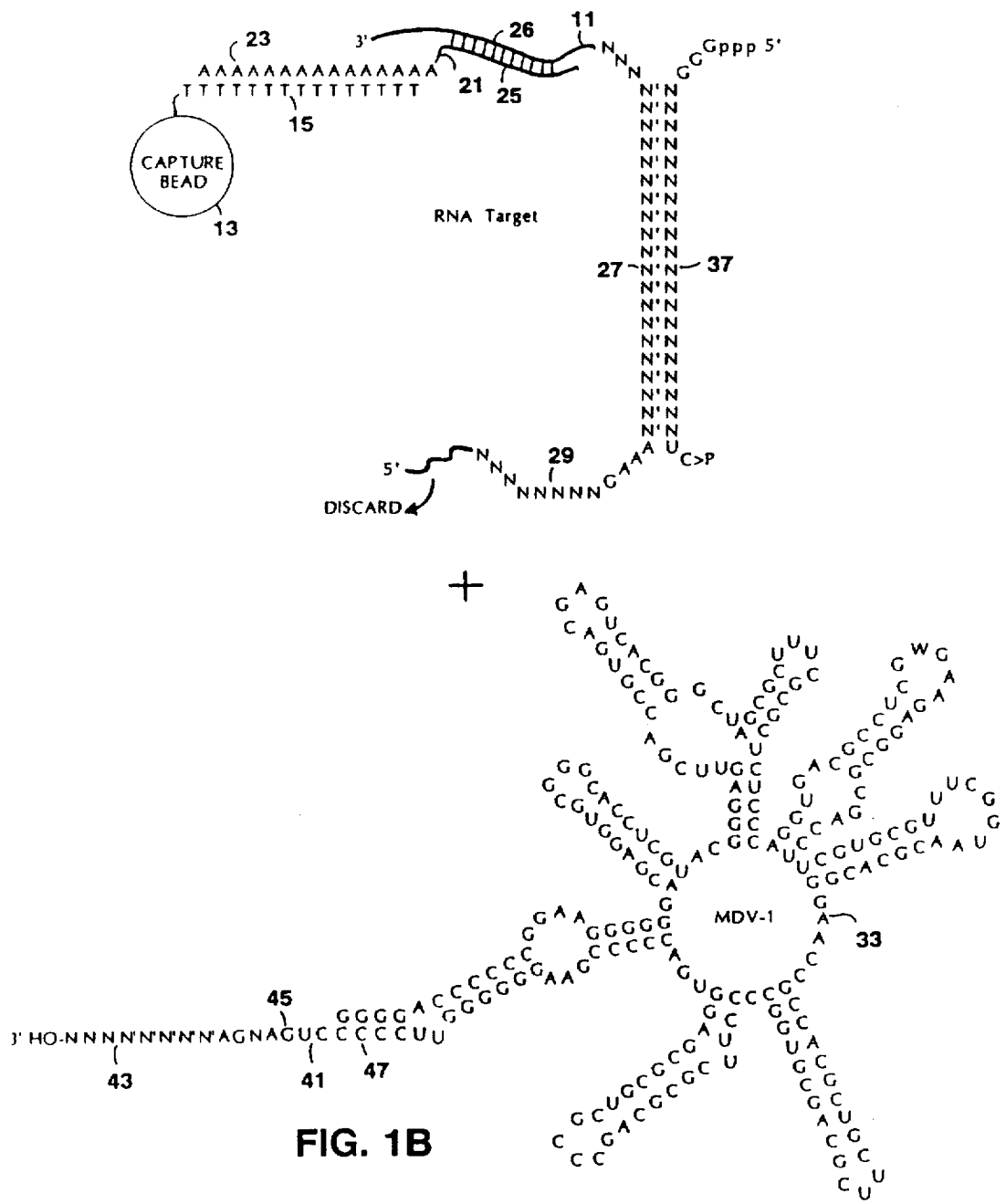

One picomole ($10^{-12}$ mol) of this RNA is hybridized to whole human blood from patients infected with human immunodeficiency virus type 1 (HIV-1), normal human blood, or a sample to be assayed for the presence of HIV-1, in a sandwich hybridization assay such as described by Ranki et al. (ibid) in the presence of 2.5M guanidine thiocyanate and one picomole of a synthetic deoxyribo-oligonucleotide having the sequence 5'-GGAAGCACA-TTGTACTGATATCTAATCCCTGGTGGTCTCATA$_{150}$-3' (SEQ ID NO:21). With general reference to FIG. 1A the hybrid is bound to a solid support by hybridization of the dA150 tract in the oligonucleotide to immobilized polydeoxythymidine such as in the well of a polystyrene microtiter place (or a capture bead as shown in FIG. 1A) coated with dT$_{3000}$ according to the methods of Collins et al., (U.S. Ser. No. 922,155 and CIP U.S. Ser. No. 136,920, fully incorporated herein by reference). The plate is incubated at 37° C. for 30 minutes after which the contents, containing unbound probes, are aspirated and discarded, and the well repeatedly washed with a buffer containing 9.5M guanidine thiocyanate. The well is then washed with a buffer containing 90 mM Tris HCl (pH7.5), and 50 µl of the same buffer except containing 14 mM MgCl$_2$ introduced into the well and incubated at 50° C. for 15 minutes to induce ribozyme cleavage. The contents of the well containing the cleaved and released probe (see FIG. 1B) are transferred to another well for replication. Five microliters of a solution containing 4 mM each ATP, GTP, CTP, and UTP, 10 µlCi of α-$^{32}$P-CTP and 1 µg of Qβ replicase are added and the plate incubated at 37° C. for 25 minutes. Two microliters of the well contents are removed and added to 18 µl of 95% formamide, 0.05% xylene cyanol, 0.05% bromphenol blue for halting replication. Five microliters of this are applied to the well of a denaturing 8% polyacrylamide gel, and the replicated RNAs resolved by electrophoresis until the xylene cyanol dye has migrated the length of the gel. An x-ray film is exposed to the gel for three hours and is then developed as the final step of detection. The larger RNA product of length equal to the number of nucleotides between the sequence corresponding to the unappended 5' terminus of the naturally-occurring MDV-1 RNA and the unappended 3' terminus of MDV-1 RNA and including the length of the sequence element inserted into the Hinf site such as described in Example 1 (in that case 10 nucleotides), indicates the presence of HIV-1 virus or its messenger RNA in the blood sample. It will also be readily recognized that by carefully timing the replication phase and comparing the results against a suitable control, correlation can be made between the amount of replicated RNA with the amount of target RNA in the original sample thereby providing quantitation results.

As will be readily understood, other methods of detecting the replicated RNA may be employed including immunological methods utilizing antibodies specific for RNA-DNA hybrids (e.g. requires addition of DNA oligonucleotides specific for replicated RNA sequence) or alternatively, using ethidium bromide, the fluorescence of which is enhanced by the presence of RNA polymers.

Example 5

An assay for target HIV-1

A pair of probes against HIV-1, the causative agent of human acquired immune deficiency syndrome, were generated. Two pairs of partially complementary oligonucleotides were generated with the sequences:

(1A) 5'-GTGTGTGTGTAAGATGTTCAGCCTGATCT-CTTACCTGTCCTATAATTTTCG-3' (SEQ ID NO:22);

(1B) 5'-AATTCGAAAATTATAGGACAGGTAAGAGAT-CAGGCTGAACATCTTACACACACAC-3' (SEQ ID NO:23);

(2A) 5'-GGGCGGTCGCGCGAAAAAGATGTTCAGCCT-GATCTCTTACCTGTCCTATAATTTTCG-3' (SEQ ID NO:24);

and (2B) 5'-AATTCGAAAATTATAGGACAGGTAAGAGAT-CAGGCTAACATCTTTTTCGCGCGACCGCCC-3' (SEQ ID NO:25).

Each of these oligonucleotide pairs (1A and 1B and 2A and 2B) were annealed and separately cloned between the EcoRI site and the SmaI site of the plasmid described as containing Fal-st insert by Lizardi et al. After cloning, the purified plasmid DNAs were restricted with EcoRI and transcribed with T7 RNA polymerase to generate two RNAs bearing 3' extensions which were in part complementary to the same sequence in HIV-1. In the RNA produced by the clone obtained with the first pair of oligonucleotides, the sequence of the replicatable RNA and the probe sequence was separated by a spacer sequence: 5"-GUGUGUGUGU-3'. In the second clone, a spacer section having the 5'-GGGCGGUCGCGCGAAA-3' was generated. Each of the RNAs was serially diluted and aliquots used to initiate Qβ replicase reactions containing 1 µg of Qβ replicase (purified according to the method of DiFrancesco disclosed in U.S. Ser. No. 07/364,306, entitled "Purification of Q-beta Replicase", filed Jun. 9, 1989 and fully incorporated herein by reference), 90 mM Tris HCl, 14 mM MgCl$_2$ and 400 µg each ATP, GTP, CTP AND UTP. After 30 minutes at 37° C., the reactions were stopped by addition of EDTA to 20 mM and ethidium bromide to 1 µg/ml. Fluorescence of the ethidium bromide-RNA complexes was observed over an ultraviolet transilluminator. Amplified product RNA was observed in reactions initiated with at least $10^4$ molecules generated by the first clone, and $10^2$ molecules generated by the second clone. These results indicate the sequence region immediately adjacent to the 3' end of the replicatable RNA sequence strongly affects the sensitivity of probe detection. Subsequent experiments indicated that increasing the reaction time did not affect the ultimate dilution yielding a detectable product by fluorescence.

These results provide practical guidance for using replicatable RNAs bearing 3' sequence extensions as probes for the sensitive detection of nucleic acids. By appropriate selection of additional sequences from the 3' end, RNA probes may be advantageously generated which have intrinsically greater sensitivity in the detection of target nucleic acid. Conversely, for some target nucleic acids which are present in an infectious agent at high levels (i.e.-ribosomal RNA, present at up to 50,000 copies per organism), additional sequences conferring relatively poor limits of detection may be utilized to advantageously avoid the background otherwise generated by the amplification of lower levels of non-specifically bound probes. For example, if reduced in number to levels at least an order of magnitude below the limit of detection using background reduction methods such as Collins (supra), non-specifically bound probes will be incapable of producing a detectable signal. Thus, the probes of the present invention comprising additional sequences from the 5' end may be used advantageously to reduce the cost, complexity, and frequency of false-positive reactions in such assays.

As will now be recognized, a number of means may be utilized to generate such constructs including the use of T4 RNA ligase and transcription of cDNA clones as described in the above example. It will be appreciated that the use of T4 RNA ligase advantageously allows the generation of constructs in which the probe extension is either RNA or DNA.

Since Qβ replicase initiates synthesis of the daughter strand at the 3' end of MDV-1 RNA template and generally continues to copy the template in a 3' to 5' direction (of the template) until the 5' terminus is reached, template molecules bearing 5' extensions will generate daughter strand products (e.g. a minus strand of template) bearing 3' terminal extensions, which in turn will be replicated as observed above (e.g. the Q-beta replicase will ignore the 3' sequences appended to the end). As will be apparent to those skilled in the art, such probes may also be employed in hybridization assays. As will now be additionally apparent, the effect of the additional sequences at the 5' end may similarly be employed to advantageously adjust the sensitivity of such probes.

An important advantage issued from the present discovery which has additional application for smart probe systems which employ the target-directed cleavage of 5' or 3' sequence extensions, since such methods need not provide for the precise and complete removal of those sequences. For example and as set forth in U.S. Ser. No. 252,243, a probe may be generated bearing both 3' and 5' extensions whose hybridization to target produces a ribozyme structure which directs cleavage of the 5' extension from the RNA. A short 3' extension remains on the molecule.

A most preferred embodiment of the present invention is diagrammed in FIG. 4, wherein a probe molecule bearing an extension is hybridized to target in solution. Shortly before, after, or simultaneously therewith, a second oligonucleotide probe is hybridized to the target adjacent to the first probe. The second oligonucleotide probe is ideally coupled to a nuclease which requires a cofactor (for example, a divalent cation) for its activity. Following hybridization, the complex is captured on a solid support in a manner such as that described by Rankmi et al. (supra), Soderlund (supra), Stabinsky (supra), and/or Syvanenen (supra). After separating, such as by washing away, the bulk of non-specifically bound probes, the cofactor for nuclease activity is added. The nuclease, coupled to the terminus of the probe proximal to the first probe when hybridized to its target, cleaves the spacer on the first probe, thereby releasing a replicatable moiety into solution. As previously indicated, the third section may be advantageously selected to maximally inhibit replication until cleavage occurs. Other variations of this approach will become apparent. For example, such probe parts may include a replicatable RNA instead bearing a 5' extension and a nuclease-coupled probe in which the ribozyme sequence is present 5' to the probe sequence element. Any of a number of nucleases may be advantageously employed as the release means. For example, micrococcal nuclease may be used since it does not cleave MDV-1 RNA (Hill & Blumenthal (1983) Nature 301, 350–352). Corey & Schultz (1987) Science 238:1401–1403, teach the construction of such oligonucleotide-micrococcal nuclease conjugates. Any number of ribozymes with endonucleolytic cleavage activity, such as those described by Haselhoff & Gerlach (Nature 3343:585–591 (1988)), Uhlenbeck (1987) Nature 328, 596–600, Ruffner (1990) Biochemistry 29,10695–10702, Cech (European pat. Appl. WO 88/04300, June 1988), Sharmeen et al. (1989) J. Virol. 63, 1428–1430; or Hampel & Tritz (1988) J. Cell. Biochem., Suppl. 12D, Abst. #N212, p.31, may be employed. Ribozymes possess a significant advantage in that the second probe bearing the ribozyme may be efficiently produced in a single step by transcription of a DNA oligonucleotide of appropriate sequence such as is described by Milligan (supra), thus reducing the cost and labor required to generate such reagents. Moreover, ribozymes tend to produce specific cleavage events, leading to a product RNA with defined replication properties.

In the specific case where the target is RNA, release means may be a small DNA oligonucleotide (for example, six nucleotides) complementary to a portion of the second sequence section of the first nucleic acid. In this case, the cleavage is ideally effected by the addition of RNase H (which acts to cleave RNA in RNA:DNA heteroduplexes) to the solution in contact with the support bearing the complex. Naturally, the means for capturing the RNA target should ideally avoid generation of such heteroduplexes in order for the cleavage event to be specific. For example, a biotinylated RNA complementary to another portion of the target RNA may be conveniently captured upon an immobilized streptavidin support.

In the specific case where the target is DNA, digestion of the sequence extension of hybrids with target may be effected directly by the addition of RNase H, without the requirement for a second probe bearing such an oligonucleotide.

Example 6

Detection of *Chlamydia trachomatis* RNA

Two oligonucleotides having the sequences: (1) 5'-AATTCTATGTGATATCAGCTAGTTGGTGGGGTAAAGGCCT-3' (SEQ ID NO:28); and (2) 5'-AATTAGGCCTTTACCCCACCAACTAGCTGATATCACATAG-3'

(SEQ ID NO:29) were annealed and ligated into a MDV cDNA construct similar to that described by Lizardi (supra), which had been digested with EcoRI. This cDNA clone differed from those described by Lizardi et al. in that the internal insert encoded a binding site for the coat protein for phage R17. This cDNA was obtained from F. R. Kramer, Public Health Research Institute, N.Y. The oligonucleotides were ligated in the orientation such that upon subsequent digestion with EcoRI, cleavage occurred downstream of the oligonucleotide with respect to the promoter for T7 RNA polymerase. The digested plasmid was transcribed in vitro with T7 RNA polymerase under the conditions described by Mulligan et al. (supra), and the transcription product of correct length isolated by electrophoresis through polyacrylamide gels containing 8.3M urea.

A capture oligonucleotide having the sequence: 5'-TACACCGCTATAAACCCGTAGGCTCATTGCAATT-TC-3' (SEQ ID NO:30) complementary to a region in the 16S ribosomal RNA of Chlamydia (Palmer et al., Chlamydial Infections (Oriel et al., eds) Cambridge Univ. Press, 1986, pp. 89–92) was synthesized and tailed with 150 dA residues using terminal deoxynucleotidyl transferase (Supertechs) as described by Collins (supra).

Various numbers of formalin-fixed elementary bodies of *Chlamydia trachomatis* were lysed in a solution of 9.0 mg/ml proteinase K (Boehringer Mannheim) and 1.6% Sarkosine (Sigma) at 65° C./for 15 minutes in a final volume of 35 μl. Thirty-five μl of a buffer containing 340 ng/ml of tailed capture oligonucleotide and 100 ng/ml of the transcription product probe was then added and solution phase hybridization allowed to occur for 30 minutes at 37° C. Fifty μl of a 0.06% (w/v) suspension of oligo-dT derivitized magnetic beads prepared according to Collins (supra) in 4% BSA, 10 mM EDTA, 0.2% Sarkosine, 9.1 M Tris-HCl pH8.0 and 0.05% bronopol was then added and incubated for an additional 5 minutes at 37° C. to capture the target-probe hybrids on the beads.

Following capture, 0.2 ml of a "was solution" containing 1M guanidine thiocyanate (GUSCN, Fluka), 10 mM EDTA, 0.04M Tris-HCl pH7.8, 0.5% Sarkosine, 0.2% BSA and 0.1% antifoam (Thomas) at 37° C. was added. The tubes were vortexed and then placed in a magnetic field (preferably such as that described in U.S. Ser. No. 121,191, entitled "Magnetic Separation Device and Methods for Use," fully incorporated herein by reference). The beads were drawn to the side of the tubes and the liquid phase removed from the tubes by aspiration. Another 0.2 ml of warm wash solution was added, the beads were resuspended by vortexing, and the beads recollected in the magnetic field. The beads were washed an additional time with another aliquot of wash solution.

The collected beads, freed of supernatant, were then resuspended in 50 μl of a buffer containing 3.25M GuSCN, 65 mM EDTA, 0.04M Tris-HCl, pH7.0, 0.5% Sarkosine, and 0.5% BSA, and incubated at 37° C. for 5 minutes to release the target-MDV probe-capture probe hybrids. The magnetic beads were collected as before, and the supernatants removed and transferred to a fresh set of tubes, each containing 50 μl of a fresh bead suspension to recapture the hybrids as described above. These beads were washed three times in the same manner as the first set, the hybrids released and recaptured by a third set of beads. This set of beads was washed three times in the same manner, and additionally, three times with 0.2 ml of a solution containing 0.1M KCl, 1 mM EDTA, 10 mM Tris-HCl, pH8.0, 0.5% NP-40.

The collected, washed beads were resuspended in 50 μl of a buffer consisting of 10 mM Tris-HCl, pH8.0, 1 mM EDTA, and 0.5% NP-40, and incubated at 37° C. for 5 minutes to elute the complexes. The beads were collected with a magnetic field, and the supernatants containing the eluted complexes transferred to a fresh set of tubes.

Ten μl of each of the bead elutes was added to a set of tubes containing 13 μl of a solution of 173 mM Tris-HCl, pH7.5, 27 mM $MgCl_2$, and 0.77 mM each ATP, GTP, CTP, and UTP (Pharmacia). Two μl of Qβ replicase (1.2 μg) purified according to DiFrancesco (supra) was added, and the tubes Incubated for 12 minutes at 37° C. Five μl of 20 mM EDTA, 32 μg/ml propidium iodide (Sigma was then added to stop replication. Fifty μl of each stopped reaction was transferred to separate wells of a U-bottomed microtiter place (Nunc). The plate was photographed over an ultraviolet transilluminator whose emission maximum was 365 nm onto Polaroid type 667 film using a Wratten #29 filter. The exposure was adjusted to minimize the apparent fluorescence in a control well containing reaction buffer and propidium iodide alone. The above assay was performed with triplicate samples of each elementary body dilution. The results are summarized in the table below. The number of "+" symbols reflects the relative fluorescence observed. "–" indicates the fluorescence did not exceed that of the control wells.

| | Fluorescence Hybridization Reaction: | | |
|---|---|---|---|
| Elementary bodies | a | b | c |
| $10^5$ | +++++ | ++++++ | +++++ |
| $10^4$ | ++++ | ++++ | +++++ |
| $10^3$ | +++ | +++ | + |
| $10^2$ | ++ | ++++ | – |
| 10 | – | – | – |
| 1 | – | – | – |
| 0 | – | – | – |

As observed in the above experiment, the assay had a sensitivity of approximately $10^3$ elementary bodies.

Example 7

Detection of HIV-1 mRNA

The assay of Example 6 was repeated, except that the capture probe was substituted with three probes complementary to conserved regions in HIV-1 RNA. The detector MDV probe was as described in Example 1 and contained the spacer sequence 5'-GGGCGGUCGCGCGAAA-3' (SEQ ID NO:27). This assay showed a sensitivity of 1000 HIV-1 RNA molecules.

Example 8

Selection of probes containing optimally replicating spacer sequences

A library of template DNAs can be generated by synthesis of an oligonucleotide having in 5' to 3' order: (1) a short (for example, 40 nucleotides) sequence identical to target, (2) a short stretch (15 nucleotides) of random sequence, and (3) a sequence complementary to the 3'-most 30 nucleotides of MDV-1 RNA. The random sequence element may be generated with ease by addition of all four blocked nucleotides during synthesis of the oligonucleotide, a procedure easily accomplished with currently available automated synthesizers. A second oligonucleotide is then synthesized which is complementary to the nineteen 5'-most nucleotides of the first oligonucleotide. This is annealed to the first oligonucleotide and extended with a DNA-dependent DNA polymerase to produce a double-stranded DNA fragment. This fragment is then cleaved with the restriction enzyme Bst EII and the cleavage product ligated to a fragment of a MDV cDNA clone such as described by Lizardi (supra), previously cleaved with Bst EII. Two picomoles of the ligation product is then transcribed by T7 RNA polymerase to generate a population of RNAs containing $10^{12}$ different spacer sequences.

Molecules within the population of RNAs which most efficiently initiate replication are advantageously selected by one of two methods: electrophoretic retardation of Qβ template RNAs hybridized to their nascent initiated daughter strands (Mills et al. (1980) Biochem 19:228–236); or isolation of the stable complex formed between Qβ replicase and template RNAs which have directed initiation of a daughter strand. An example of the latter method is described below.

Two picomoles of RNAs bearing random sequence spacers is incubated with 5 picomoles (1.2 μg) of Qβ replicase for 5 minutes at 37 in 25 μl of 100 mM Tris HCl, pH7.5, 14 mM $MgCl_2$. Five μl of the same buffer containing 2.4 mM each GTP and ATP is added, and the incubation continued for an additional 5 minutes. Five μl of buffer containing 40 picomoles of MDV-1 RNA is then added and the incubation continued for 2 minutes. The reaction is chilled to 0° C. and applied to the top of a 2.2 ml 10–30% glycerol gradient in 10 mM Tris-HCl, pH7.5, 1 mM $MgCl_2$ prechilled to 0° C. The gradient is spun at 55 K RPM in a TLS-55 rotor (Beckman Instruments, Palo Alto, Calif.) for 6 hours at 4° C. The enzyme: RNA complex, which sediments 40% faster than free RNA, is collected, extracted with phenol, and ethanol precipitated. This population is enriched in RNAs which can be replicated efficiently by Qβ replicase. To further enrich this population, a cDNA library of this population is first constructed. An oligonucleotide complementary to the probe region is used to prime synthesis of a single-stranded cDNA population using reverse transcriptase (Maniatis et al., supra). A second oligonucleotide is synthesized to contain, in 5' to 3' order, (1) a restriction enzyme sequence to allow cloning of the duplex cDNA, (2) the sequence of a promoter for T7 RNA polymerase, and (3) the sequence of the first 22 nucleotides of MDV-1 RNA. This oligonucleotide and the one used for priming synthesis of the first strand cDNA product are used in a PCR reaction to generate one picomole of duplex DNA using as a template the first strand cDNA. This product is purified by native polyacrylamide gel electrophoresis, and transcribed with T7 RNA polymerase to generate an RNA population which is subjected again to the complex formation-sedimentation protocol. This process may be repeated as many times as desired, but as will be recognized, will converge upon some limiting degree of enrichment. The degree of enrichment after each cycle of selection is determined by cloning the duplex cDNAs into plasmid vectors, and examining the sensitivity of detection of the RNAs produced by transcription of several (for example, 12) such clones chosen at random from the products of each cycle of selection.

The sensitivity of detection of the cloned RNAs may be determined as follows. The plasmid DNAs from each clone is purified by standard methods. Each is restricted with a restriction enzyme immediately downstream of the cDNA and transcribed by T7 RNA polymerase to produce an RNA product devoid of vector sequence. This RNA is purified either by gel electrophoresis or by capture onto oligo dT-magnetic beads as in the method described in Example 2 with a DNA oligonucleotide of the same sequence as the target tailed with $dA^{150}$, except that a second capture probe is omitted. Each of the purified transcripts is serially diluted in water and aliquots (10 μl) added to Qβ reactions as described in Example 2. The reactions are allowed to run 30 min. at 37° C., stopped, and the minimum number of probes required to observe product determined by the highest dilution producing fluorescence. This process is repeated for clones obtained from each round of the selection process.

It will be readily appreciated that the above process may also be applied to the isolation of RNAs which replicate efficiently when hybridized to target. This is simple performed by first hybridizing the population of RNAs to a synthetic target prior to the formation of initiation complexes. As will also be recognized, members of such a population may contain molecules which replicate more efficiently when hybridized to target than when free. Such molecules will be preferred probes for use in hybridization assays since the molecules non-specifically carried through the hybridization process will be intrinsically less efficiently replicated.

Example 9

A smart probe system for the detection of HIV-1 RNA

An oligonucleotide of the sequence: 5'-AATTCTTTAAAAAATCATAGGACAGGTAAGAGATCAAGCTGAACATCTTGGAGGGACTGTCAGGACAAAAGGGAACCCCCCTTCGGGGG-3' (SEQ ID NO:31) is synthesized. A second oligonucleotide of the sequence: 5'-GTGACCCCCCGAAGGGGGGTTCCCTTTTGTCCTGACAGTCCCTCCAAGATGTTCAGCTTGATCTCTTACCTGTCCTATGATTTTTTAAAG-3' (SEQ ID NO:32) is synthesized. The two oligonucleotides are annealed and ligated into a cDNA clone of a recombinant MDV RNA as described by Lizardi (supra) and previously digested with BsEII and EcoRI. The resultant clone is digested with Dra I and transcribed with T7 RNA polymerase. The product RNA is purified on an 6% polyacrylamide gel containing 8.3M urea, and eluted from the gel after visualization either by autoradiography or UV shadowing. A template oligonucleotide having the sequence: 5'-TACCAGGTAATATACCACAACGTGTGTTTCTCTGGTTGACTTCTCTGTTTGGGGGGGAGACAGCAGTACAAATGGCAGTATTCATCCACAATTTTCCCTATAGTGAGTCGTATTAAT-3' (SEQ ID NO:33) for a ribozyme-probe is synthesized. Two picomoles of this product is annealed to an equimolar amount "T7 promoter-primer" oligonucleotide (Promega) and transcribed by T7 RNA polymerase as described by Milligan (supra), except that $\alpha$-$^{32}$ CTP (1 Ci/mmol) is included in the reaction in order to label the product for visualization by auto radiography. The transcription product is purified on a 10% poly acrylamide gel containing 8.3M urea and eluted. One nanogram of each of the above RNAs is added to a HIV-1 assay as described in Example 7. After washing the beads for the final time as described in Example 6, the beads are resuspended in 50 μl of an elution buffer containing 200 mM KCl, 10 mM $MgC_{12}$, and 0.5% NP-40. The beads are incubated in this buffer at 37° C. for 10 minutes, and then recollected by placing in a magnetic field. The liquid phase is collected and transferred to a fresh tube. The RNA present in 10 μl of this elute is amplified in a Qβ reaction as described in Example 6.

Example 10

Identification of probe molecule sequences conferring greatest differential replicability between cleaved and uncleaved forms.

Portions of the sequence of the "hairpin" ribozyme (that comprising section 45 and 35 in FIG. 3) may be altered without significantly affecting cleavage, as long as such changes are accompanied by alterations which preserve the ability of those sequences to base-pair with their complementary elements. In particular, it has been shown that the sequence elements UGAC (SEQ ID NO:34) and CUGUUU (SEQ ID NO:35) in portion 35 may be altered as long as the sequences in section 45 shown paired to those elements are altered to retain base pairing. In addition, the adenosine following the UGAC (SEQ ID NO:34) element can be changed to any nucleotide without significant effects on catalytic activity.

Since the nucleotide sequence of this region has strong effects on the replication of a midivariant probe bearing a 3' terminal extension (see Example 5), and since cleavage of an RNA such as shown in FIG. 3 would leave a five nucleotide 3' extension which in some cases may strongly inhibit replication, sequences which would allow the most efficient replication after cleavage were sought.

Two oligonucleotides having the sequences: (1) 5'-GTGACCCCCCAGGGGGGTTCCCNNNNNGTCNN-NNNNCATCCCAAGATGTTCAGCTTGATCTCTTACC-TGTCCTATG-3' (SEQ ID NO:36), and (2) 5'-AATT-CATAGGACAGGTAAGAGATCAAGCTGAACATCTT-GGGATGNNNNNNGACNNNNNGGGAACCCCCCTT-CGGGGG-3' (SEQ ID NO:37) were synthesized, where N=equimolar mixture of all four nucleotides from the group A, G, C or T. Thus, each oligonucleotide actually represents a population of DNAs, each having a unique sequence in that region. The oligonucleotides were annealed and ligated into the large fragment of a cDNA transcription clone of a variant of MDV-1 which is capable of replicating efficiently in the presence of the intercalating dye, propidium iodide [see, by way of example, Stefano, U.S. patent application Ser. No. 07/514,518], produced by restriction with BstEII and EcoRI. The oligonucleotides reconstruct a 24 nucleotide portion of the sequence of the MDV variant, and append the MDV sequence with first a region comprising a portion of the hairpin ribozyme followed (in the 5' to 3' sense) a sequence complementary to the pol region of HIV-1. Competent *E. coli* cells (DH5-α Bethesda Research Laboratories) were transformed with the ligation mixture, and grown overnight in liquid culture in the presence of 100 μg/ml ampicillin. Plasmid DNA was isolated by standard methods, and used to transform another aliquot of competent *E. coli* cells, which were plated on selective media. This insured that each clone represented a unique sequence in the region in which random nucleotides were inserted.

Plasmid DNAs prepared from one hundred individual clones were restricted separately with either EcoRI or FokI. Cleavage of the DNAs with FokI yielded, upon transcription of the clones with T7 RNA polymerase, RNAs bearing 5 nucleotide 3' extensions, the 3' terminus of which correspond to the site of cleavage of a complementary hairpin ribozyme catalytic sequence group. Each clone contained a different sequence in this region corresponding to the particular sequence of the random sequence element in the oligonucleotide(s) above. Each of the cleaved preparations was transcribed with T7 RNA polymerase in the presence of α-[$^{32}$P]-CTP essentially as described by Milligan et al., and the product RNAs were purified by electrophoresis through 6% polyacrylamide gels containing 8.3M urea. The RNAs were eluted from the gels (Maniatis et al. A Cloning Manual.), quantiated by counting a portion in a scintillation counter, and serially diluted. The diluted RNAs (5 μl) were added 50 μl of a reaction mixture containing 90 mM Tris-HCl (pH7.8), 15 mM $MgCl_2$, 9.4 mM each ATP, GTP, CTP and UTP, 3.2 μg/ml propidium iodide and 2 μg Qβ replicase in a 96-well microtiter place at 0° C. The plate was warmed to 37° by placing over an aluminum block kept at that temperature, and allowed to incubate for a total of 40'. The reactions were then stopped by addition of 25 μl of 80 mM EDTA. The plates were placed over a long-wave ultraviolet transilluminator. Presence of a strong orange-pink fluorescence indicated presence of amplified product RNA. Each of the RNAs showed characteristic limits of detection, depending upon the sequence and length of the 3' extension. Two such RNAs gave rise to amplified product when only 1–10 molecules were added to the Qβ replicase reaction. Other clones gave rise to RNAs requiring up to 1000 molecules to observe any product RNA. The DNAs of the optimally-replicating RNAs and several others were sequenced.

As determined from the sequencing of the cloned plasmid DNA, one of the two optimally-replicating RNAs possessed a 3' terminal extension 5'-AUGAA-3' (SEQ ID NO:38). A second library was constructed by ligation of the annealed mixture of pair of two new oligonucleotides having the sequences: (3) 5'-GTGACCCCCCGAAGGGGGGTTCC-CATGAAGTCNNNNNNMGATGTTCAGCTTGATCTCT-TACTTGTTCTAAGGTAAGAGAATTCGGGCCCGGTA-C-3' (SEQ ID NO:39), and (4) 5'-CGGGCCCGAATTCTC-TTACCTTAGAACAAGTAAGAGATCAAGCTGAACAT-CTTNNNNNNGACTTCATGGGAACCCCCCTTCGGG-GG-3' (SEQ ID NO:40). These were inserted between the BstEII site and the Kpn site of the MDV transcription vector used above. The transformation and screening was similar to that described above, except the clones were restricted with EcoRI prior to transcription with T7 RNA polymerase. In this case, the RNAs produced comprise a 222 nucleotide MDV-1 variant RNA to which a 59 nucleotide 3' extension is appended which begins with the sequence AUGAA. Thirty of these RNAs were characterized according to their ability to replicate with Qβ replicase as described above. Most of the RNAs required 1000 to 10,000 molecules to see any amplified product. However, three of the RNAs required one million or more molecules to observe any amplification product within 40 minutes. Two of those clones were sequenced. The sequence of the varied element was 5'-CAUUAC-3' (SEQ ID NO:41) in one RNA and 5'-UUUACG-3' (SEQ ID NO:42) in the other. Each of these sequences shows limited complementarity to a portion of the MDV-1 RNA in the single-stranded region about nucleotide 100, which is previously identified as the center of a region with which Qβ replicase strongly interacts. Allowing base-pairing between G and U residues, a consensus sequence for the inhibitory sequence of the 3' extension would be UUYRC (SEQ ID NO:43), where Y (pyrimidine) is either U or C, and R (purine) is either G or A.

The screening reactions were performed in the presence of 3.2 μg/ml of propidium iodide. The response of each RNA was reassessed in the presence of 0, 1.5, and 3.2 μg/ml of propidium iodide in reactions identical to those described above. The RNA bearing the CAUUAC (SEQ ID NO:41) element required E3, E5, and E7 molecules to observe amplified product with Qβ replicase in 40' in the presence of 0, 1.5, and 3.2 μg/ml propidium iodide, respectively. The RNA bearing the UUUACG (SEQ ID NO:42) element required E4, E5, or E6 molecules to observe amplification products in the presence of 0, 1.5, or 3.2 μg/ml propidium iodide. This indicates that the intercalating agent, propidium iodide, plays a role in the mechanism of inhibition by these sequence elements, and is required for the inhibition.

To obtain a ribozyme probe for the RNA bearing the CAUUAC (SEQ ID NO:41) element, an oligonucleotide having the sequence: 5'-TACCAGGTAATATAC-CACAACGTGTGTTTCTCTGGTATGATTCTCATTACG-AGACAGCAGTACAAATGGCAGTATTCATCCACAAT-TTTCCCTATAGTGAGTCGTATTAAT-3' (SEQ ID NO:44)

was synthesized. This was annealed to an oligonucleotide of the sequence 5'-ATTAATACGACTCACTATAGGG-3' (SEQ ID NO:45) ("T7 Promoter-Primer", Promega Sciences, Madison, Wis.) and transcribed with T7 RNA polymerase under conditions described by Milligan et al. (ibid), and the product RNA purified by denaturing polyacrylamide gel electrophoresis. This yielded an RNA of the sequence: 5'GGGAAAAUUGUGGAUGAAUACUG-CCAUUUGUACUGCUGUCUCGUAAUGAGAAUCAU-ACCAGAGAAACACACGUUGUGGUAUAUUACCUG-GUA-3' (SEQ ID NO:46). When annealed to HIV target nucleic acid with the MDV probe-bearing the CAUUAC (SEQ ID NO:41) inhibitory sequence element, the structure similar to that represented in FIG. 3 is obtained.

To test for the cleavage activity, 10 fmol of $^{32}$P-labelled midivariant probe and 100 fmol ribozyme probe were annealed to 1 ng of a synthetic HIV target RNA, and the hybrid complexes isolated by reversible target capture on magnetic particles, as generally described in GENE-TRAK Systems HIV assay, which assay is commercially available, except that only two rounds of capture and release were performed. After washing the final magnetic particles to which the complexes were immobilized with 0.3M KCl as described, the particles were resuspended 100 μl 0.05M Tris-HCl, pH7.8, 15 mM MgCl$_2$, and 0.5% NP-40, and incubated at 37° C. for 15 minutes. The particles were removed from solution by placing in a magnetic field, and the supernatant removed and counted. Twenty seven percent of the cpm initially bound to the particles was released into solution, compared to less than one percent in a control reaction in which the ribozyme probe was omitted.

Example 11
Affinity-ligand modification probes to improve signal to noise ratios.

Specific placement of an affinity ligand on the portion of a cleavable midivariant probe which is distal to the cleavage directed by the release agent would allow an additional degree of discrimination of target-bound from non-hybridized probes. Briefly, the 3' terminal region of the midivariant probe such as that described in Example 10 is derivatized with biotin, poly rA or other ligand. Following hybridization with target nucleic acid, the derivatized kprobe is captured on a receptor-derivatized solid support irrespective of whether it is target-associated or not. Cleavage by the ribozyme or other release agent specifically releases only those probes which are target-associated into solution. This approach has the advantage that a high affinity ligand:receptor interaction (i.e. -biotin: avidin) may be used, and that capture is directed at the entire population of probe molecules.

As will be recognized by those familiar to the art, several methods may be used to specifically label the 3' terminal region of the probe molecule. These include, but are not limited to: (1) ligating a small RNA or DNA oligonucleotide produced synthetically, containing one or more biotin ligands, to the 3' terminus with T4 RNA ligase; (2) addition of an RNA tail to the 3' terminus with E. coli poly A polymerase, using biotinylated ribonucleoside triposphates; (3) periodate oxidation of the 3' terminal residue followed by coupling to a biotinylated ligand bearing a side chain having a primary amine followed by reduction; and, (4) hybridization of a biotinylated complementary RNA to a region distal (e.g. -3' to) the target-binding region of the midivariant probe. As will also be recognized, other ligand:receptor systems may be used, although biotin:avidin is preferred for its high affinity. These systems include, but are not limited to: (a) poly rA: poly T interactions or other hybrid-forming nucleic acids (b) specific RNA binding proteins such as the coat protein of R17, and (c) high affinity antibody:antigen interactions, such as fluorescein:antifluorescein.

The following example demonstrates the use of a biotinylated cRNA to specifically label the 3' end of a cleavable midivariant probe. Two oligonucleotides are synthesized: (1) 5'-GAGCTCGAATT CACTGGCCGTC-3' (SEQ ID NO:47) and (2) 5'-CCCCCCGGCGCCTTATTAAT-ACGACTCACTATAGGGCATTCGCCATTCAGGCTG-3' (SEQ ID NO:48). One hundred pmol of each of the oligonucleotides are mixed with 1 fmol of pUC19 linearized with HindIII, in a PCR reaction containing 1 U of Taq or other thermostabile DNA polymerase. The mixture is subjected to twenty-five cycles of replications, and the 208 bp amplification product purified by electrophoresis through a non-denturing gel. The product is transcribed with T7 RNA polymerase, substituting biotin-14-UTP (Enzo) for UTP in the reaction, producing a 155 nucleotide RNA. The product is purified by gel filtration or electrophoresis through a non-dentaturing polyacrylamide gel.

A midivariant probe bearing a long 3' terminal extension complementary to the biotinylated RNA is generated by restricting the midivariant clone containing the inhibitory sequence as described in Example 10 with Kas I instead of EcoRI prior to transcription with T7 RNA polymerase. This yields an RNA bearing a 3' terminal sequence complementary to nucleotides 235–412 of pUC19 which includes the sequence of the biotinylated cRNA.

A hybridization reaction containing 100 fmol of the ribozyme probe from Example 10, 10 fmol of the transcription product from the KasI-restricted DNA, 100 fmol of the biotinylated cRNA, and various amounts of synthetic HIV target are combined with poly(dA)-tailed capture probes in 2.5M GTC. After 30 minutes of hybridization, the complexes are captured onto oligo dT$_{14}$-derivatized paramagnetic particles as generally described in GENE-TRAK Systems HIV assay, which assay is commercially available. The particles are separated from the solution by placing the tubes in a magnetic field, the supernatants removed, and the particles washed three times with a buffer containing 1M GTC. The complexes are released by placing the particles in 2.75M GTC at 37° C. for 5 minutes. The particles are removed, and the supernatant added to a suspension of streptavidin-derivatized paramagnetic particles (Advanced Magnetics, Cambridge, Mass.). The suspension is incubated 5 minutes at 37° C., the particles separated from the solution in a magnetic field as above, washed three times with 200 μl of 0.1M KCl, 1 mM EDTA, 0.5% NP-40, and 0.05M Tris-HCl pH7.8. After washing, the particles are suspended in 100 μl of 15 mM MgCl$_2$, 0.5% NP-40, 0.05M Tris-HCl, pH7.8 and incubated 15 minutes at 37° C. The released midivariants are amplified by mixing 50 μl of the supernatant from the above reaction with 50 μl of a solution containing 2 ∥g of Qβ replicase, 800 μM each ATP, GTP, CTP, and UTP, 15 mM MgCl$_2$, and 6.4 μg/ml propidium iodide. The fluorescence displayed by the reaction is followed using a Fluoroskan instrument (Flow laboratories) or other fluorimeter capable of maintaining the reaction vessel at a constant temperature of 37°. The time at which a fluorescence increase is first detected is inversely proportional to the level of HIV target RNA added to the initial hybridization.

While the preferred embodiments have been illustrated and described, it is understood that the present invention is capable of variation and modification and, therefore, should not be limited to the precise details set forth, but should include such changes and alterations that fall within the purview of the following claims.

I claim:

1. A composition comprising first and second nucleic acids;
    said first nucleic acid comprising first, second, and third sections connected in series; wherein
        said first section comprises a nucleotide sequence which is autocatalytically replicated in the presence of an RNA-dependent RNA polymerase upon cleavage of said second section;
        said second section comprises a nucleotide sequence which is cleaved by a release means; and
        said third section comprises a nucleotide sequence which binds to a target nucleic acid; and
    said second nucleic acid comprising a first region comprising a nucleotide sequence which binds to said target nucleic acid, and a second region comprising a release means, or a portion thereof, said release means cleaving said nucleotide sequence of said second section of said first nucleic acid only when said third section of said first nucleic acid and said first region of said second nucleic acid are bound to said target nucleic acid.

2. The composition of claim 1, wherein said release means is a ribozyme.

3. The composition of claim 2, wherein said ribozyme is a hairpin ribozyme.

4. The composition of claim 2, wherein said ribozyme is a hammerhead ribozyme.

5. The composition of claim 4, wherein said ribozyme comprises nucleotides from said target nucleic acid.

6. The composition of claim 2, wherein
    (a) said second section of said first nucleic acid comprises the sequence 5'-K'UHJ-3' (SEQ ID NO:50); and
    (b) said target nucleic acid and said portion of said ribozyme in said second region of said second nucleic acid comprise either 5'-MGAAAK-3' (SEQ ID NO: 2) or 5'-J'CUGANGAM'-3' (SEQ ID NO:3), independently, wherein H is C, U, or A, N is C, U, G, or A, and the letters J, J', K, K', M, and M' each represent a group of four or more nucleotides, wherein J and J' are complementary to each other, K and K' are complementary to each other, and M and M' are complementary to each other.

7. The composition of claim 6, wherein said target nucleic acid comprises the sequence 5'-MGAAAK-3' (SEQ ID NO:2) and said portion of said ribozyme in said second region of said second nucleic acid comprises the sequence 5'-J'CUGANGAM'-3' (SEQ ID NO:3), wherein N is C, U, G, or A.

8. The composition of claim 6, wherein said target nucleic acid comprises the sequence 5'-J'CUGANGAM'-3' (SEQ ID NO:3) and said portion of said ribozyme in said second region of said second nucleic acid comprises the sequence 5'-MGAAAK-3' (SEQ ID NO:2), wherein N is C, U, G, or A.

9. The composition of claim 2, wherein said ribozyme in said second region of said second nucleic acid comprises the sequences 5'-J'CUGANGAM'-3' (SEQ ID NO:3) and 5'-MGAAAK-3' (SEQ ID NO:2), wherein N is C, U, G, or A, and the letters J, J', K, K', M, and M' each represent a group of four or more nucleotides, wherein J and J' are complementary to each other, K and K' are complementary to each other, and M and M' are complementary to each other.

10. The composition of claim 1, wherein said portion of said release means is a DNA oligonucleotide which
    (a) binds to said nucleotide sequence in said second section of said first nucleic acid when said third section of said first nucleic acid and said first region of said second nucleic acid are bound to said target nucleic acid; and
    (b) causes cleavage of said nucleotide sequence in said second section of said first nucleic acid in the presence of ribonuclease H.

11. The composition of claim 1, wherein said release means is micrococcal nuclease.

12. The composition of claim 1, wherein said RNA-dependent RNA polymerase is Q-beta replicase.

13. The composition of claim 1, wherein said autocatalytically replicable nucleotide sequence is substantially identical to MDV-1.

14. The composition of claim 1, wherein said third section further comprises a ligand which binds to an anti-ligand bound to a support.

15. The composition of claim 14, wherein said ligand is selected from the group consisting of biotin, avidin, a nucleic acid, an antibody, and an antigen.

16. The composition of claim 1, wherein said first nucleic acid further comprises an inhibitory element positioned at the end of said third section opposite from said second section, said inhibitory element interacting with a region of said sequence in said first section of said first nucleic acid.

17. The composition of claim 16, wherein said first section is substantially identical to MDV-1, and said inhibitory element interacting with said autocatalytically replicable sequence in the region corresponding to nucleotide locations 81 to 126 of MDV-1.

18. The composition of claim 17, wherein said inhibitory element comprises the sequence 5'-UUYRC-3' (SEQ ID NO:1), wherein Y is any pyrimidine, and R is any purine.

19. The composition of claim 2, wherein the end of said second region opposite from said first region, of said second nucleic acid, is linked to the end of said first section opposite from said second section, of said first nucleic acid, by a phosphodiester bond.

20. A method for detecting the presence of a target nucleic acid in a sample, said method comprising the steps of (a) contacting said sample with the composition of claim 1 to form a mixture;

(b) imposing hybridization conditions on said mixture to allow formation of a complex between the first and second nucleic acids in said composition and said target nucleic acid, if present;

(c) imposing release reaction conditions and autocatalytic replication reaction conditions on said mixture to form an autocatalytic reaction product; and (d) detecting said autocatalytic reaction product as a measure of the presence of said target nucleic acid in said sample.

21. The method of claim 20, wherein said third section of said first nucleic acid further comprises a ligand which binds to an anti-ligand bound to a support; said method further comprising the steps of binding said first nucleic acid to said support through said ligand and said anti-ligand, and separating substantially all unbound material from said support prior to imposing said release reaction conditions and said autocatalytic replication reaction conditions on said mixture.

* * * * *

SEQUENCE LISTING ( 1 ) GENERAL INFORMATION:

( i i i ) NUMBER OF SEQUENCES: 50

( 2 ) INFORMATION FOR SEQ ID NO:1:

( i ) SEQUENCE CHARACTERISTICS:
    ( A ) LENGTH: 5 base pairs
    ( B ) TYPE: nucleic acid
    ( C ) STRANDEDNESS: single
    ( D ) TOPOLOGY: linear ( i i ) MOLECULE TYPE: RNA (genomic)

( i i i ) HYPOTHETICAL: NO ( i v ) ANTI-SENSE: NO ( x i ) SEQUENCE DESCRIPTION: SEQ ID NO:1:

U U Y R C                                                             5

( 2 ) INFORMATION FOR SEQ ID NO:2:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: RNA (genomic)

( i i i ) HYPOTHETICAL: NO ( i v ) ANTI-SENSE: NO ( i x ) FEATURE:
    ( A ) NAME/KEY: misc_feature
    ( B ) LOCATION: 1..4
    ( D ) OTHER INFORMATION: /function= "the 1st 4 N's are
       complementary to last 4 N's of Seq. 3"

( i x ) FEATURE:
    ( A ) NAME/KEY: misc_feature
    ( B ) LOCATION: 9..12
    ( C ) IDENTIFICATION METHOD: experimental
    ( D ) OTHER INFORMATION: /function= "last 4 N's are
       complementary to 1st 4 N's of Seq 4"
       / evidence= EXPERIMENTAL ( x i ) SEQUENCE DESCRIPTION: SEQ ID NO:2:

NNNNGAAANN NN                                                        12

( 2 ) INFORMATION FOR SEQ ID NO:3:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: RNA (genomic)

( i i i ) HYPOTHETICAL: NO ( i v ) ANTI-SENSE: NO ( i x ) FEATURE:
    ( A ) NAME/KEY: misc_feature
    ( B ) LOCATION: 1..4
    ( D ) OTHER INFORMATION: /function= "1st 4 N's are
       complementary to bp 7-10 of Seq 4"

( i x ) FEATURE:
   ( A ) NAME/KEY: misc_feature
   ( B ) LOCATION: 12..15
   ( C ) IDENTIFICATION METHOD: experimental
   ( D ) OTHER INFORMATION: /function= "last 4 N's are
       complementary to bp 1-4 of Seq 1"
       / evidence= EXPERIMENTAL ( x i ) SEQUENCE DESCRIPTION: SEQ ID NO:3:

NNNNCUGANG ANNNN    15

( 2 ) INFORMATION FOR SEQ ID NO:4:

( i ) SEQUENCE CHARACTERISTICS:
       ( A ) LENGTH: 10 base pairs
       ( B ) TYPE: nucleic acid
       ( C ) STRANDEDNESS: single
       ( D ) TOPOLOGY: linear ( i i ) MOLECULE TYPE: RNA (genomic)

( i i i ) HYPOTHETICAL: NO ( i v ) ANTI-SENSE: NO ( i x ) FEATURE:
       ( A ) NAME/KEY: misc_feature
       ( B ) LOCATION: 1..4
       ( C ) IDENTIFICATION METHOD: experimental
       ( D ) OTHER INFORMATION: /function= "1st 4 N's are
           complementary to bp 9-12 of Seq 1"
           / evidence= EXPERIMENTAL ( i x ) FEATURE:
       ( A ) NAME/KEY: misc_feature
       ( B ) LOCATION: 7..10
       ( D ) OTHER INFORMATION: /function= "bp 7-10 are
           complementary to bp 1-4 of Seq 3"

( x i ) SEQUENCE DESCRIPTION: SEQ ID NO:4:

NNNNUMNNNN    10

( 2 ) INFORMATION FOR SEQ ID NO:5:

( i ) SEQUENCE CHARACTERISTICS:
       ( A ) LENGTH: 12 base pairs
       ( B ) TYPE: nucleic acid
       ( C ) STRANDEDNESS: single
       ( D ) TOPOLOGY: linear ( i i ) MOLECULE TYPE: RNA (genomic)

( i i i ) HYPOTHETICAL: NO ( i v ) ANTI-SENSE: NO ( i x ) FEATURE:
       ( A ) NAME/KEY: misc_feature
       ( B ) LOCATION: 1..4
       ( C ) IDENTIFICATION METHOD: experimental
       ( D ) OTHER INFORMATION: /function= "bp 1-4 are
           complementary to bp 9-12 of Seq 6"
           / evidence= EXPERIMENTAL ( i x ) FEATURE:
       ( A ) NAME/KEY: misc_feature
       ( B ) LOCATION: 9..12
       ( C ) IDENTIFICATION METHOD: experimental
       ( D ) OTHER INFORMATION: /function= "bp 9-12 are
           complementary to bp 1-4 of Seq 6"
           / evidence= EXPERIMENTAL ( x i ) SEQUENCE DESCRIPTION: SEQ ID NO:5:

NNNNNGUCNN NN    12

( 2 ) INFORMATION FOR SEQ ID NO:6:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: RNA (genomic)

( i i i ) HYPOTHETICAL: NO ( i v ) ANTI-SENSE: NO ( i x ) FEATURE:
        ( A ) NAME/KEY: misc_feature
        ( B ) LOCATION: 1..4
        ( C ) IDENTIFICATION METHOD: experimental
        ( D ) OTHER INFORMATION: /function= "bp 1-4 are
            complementary to bp 9-12 of Seq 5"
            / evidence= EXPERIMENTAL ( i x ) FEATURE:
        ( A ) NAME/KEY: misc_feature
        ( B ) LOCATION: 9..12
        ( D ) OTHER INFORMATION: /function= "bp 9-12 are
            complementary to bp 1-4 of Seq 5"

( x i ) SEQUENCE DESCRIPTION: SEQ ID NO:6:

NNNNAGAANN NNACCAGAGA AACACACGUU GUGGUAUAUU ACCUGGUA    48

( 2 ) INFORMATION FOR SEQ ID NO:7:

( i ) SEQUENCE CHARACTERISTICS:
        ( A ) LENGTH: 4 base pairs
        ( B ) TYPE: nucleic acid
        ( C ) STRANDEDNESS: single
        ( D ) TOPOLOGY: linear ( i i ) MOLECULE TYPE: RNA (genomic)

( i i i ) HYPOTHETICAL: NO ( i v ) ANTI-SENSE: NO ( x i ) SEQUENCE DESCRIPTION: SEQ ID NO:7:

GAAA    4

( 2 ) INFORMATION FOR SEQ ID NO:8:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear ( i i ) MOLECULE TYPE: RNA (genomic)

( i i i ) HYPOTHETICAL: NO ( i v ) ANTI-SENSE: NO ( x i ) SEQUENCE DESCRIPTION: SEQ ID NO:8:

CUGANGA    7

( 2 ) INFORMATION FOR SEQ ID NO:9:

( i ) SEQUENCE CHARACTERISTICS:
        ( A ) LENGTH: 7 base pairs
        ( B ) TYPE: nucleic acid
        ( C ) STRANDEDNESS: double
        ( D ) TOPOLOGY: linear (  i  i  ) MOLECULE TYPE: DNA (genomic)

(  i  i  i  ) HYPOTHETICAL: NO (  i  v  ) ANTI-SENSE: NO (  x  i  ) SEQUENCE DESCRIPTION: SEQ ID NO:9:

CTCTTCN  7

( 2 ) INFORMATION FOR SEQ ID NO:10:

(  i  ) SEQUENCE CHARACTERISTICS:
        ( A ) LENGTH: 10 base pairs
        ( B ) TYPE: nucleic acid
        ( C ) STRANDEDNESS: double
        ( D ) TOPOLOGY: linear (  i  i  ) MOLECULE TYPE: DNA (genomic)

(  i  i  i  ) HYPOTHETICAL: NO (  i  v  ) ANTI-SENSE: NO (  x  i  ) SEQUENCE DESCRIPTION: SEQ ID NO:10:

CCCCTGANGA  10

( 2 ) INFORMATION FOR SEQ ID NO:11:

(  i  ) SEQUENCE CHARACTERISTICS:
        ( A ) LENGTH: 4 base pairs
        ( B ) TYPE: nucleic acid
        ( C ) STRANDEDNESS: double
        ( D ) TOPOLOGY: linear (  i  i  ) MOLECULE TYPE: DNA (genomic)

(  i  i  i  ) HYPOTHETICAL: NO (  i  v  ) ANTI-SENSE: NO (  x  i  ) SEQUENCE DESCRIPTION: SEQ ID NO:11:

GATC  4

( 2 ) INFORMATION FOR SEQ ID NO:12:

(  i  ) SEQUENCE CHARACTERISTICS:
        ( A ) LENGTH: 5 base pairs
        ( B ) TYPE: nucleic acid
        ( C ) STRANDEDNESS: double
        ( D ) TOPOLOGY: linear (  i  i  ) MOLECULE TYPE: DNA (genomic)

(  i  i  i  ) HYPOTHETICAL: NO (  i  v  ) ANTI-SENSE: NO (  x  i  ) SEQUENCE DESCRIPTION: SEQ ID NO:12:

CCCGA  5

( 2 ) INFORMATION FOR SEQ ID NO:13:

(  i  ) SEQUENCE CHARACTERISTICS:
        ( A ) LENGTH: 4 base pairs
        ( B ) TYPE: nucleic acid
        ( C ) STRANDEDNESS: double
        ( D ) TOPOLOGY: linear (  i  i  ) MOLECULE TYPE: DNA (genomic)

(  i  i  i  ) HYPOTHETICAL: NO ( i v ) ANTI-SENSE: NO ( x i ) SEQUENCE DESCRIPTION: SEQ ID NO:13:

GGGG 4

( 2 ) INFORMATION FOR SEQ ID NO:14:

( i ) SEQUENCE CHARACTERISTICS:
        ( A ) LENGTH: 4 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:14:

GGCC 4

( 2 ) INFORMATION FOR SEQ ID NO:15:

( i ) SEQUENCE CHARACTERISTICS:
        ( A ) LENGTH: 31 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: misc_feature
        ( B ) LOCATION: 3..4
        ( D ) OTHER INFORMATION: /function= "N=any nucleotide
            having the sequence of Seq 16"

( x i ) SEQUENCE DESCRIPTION: SEQ ID NO:15:

TCNTCAGGGG GCCCTATAGT GAGTCGTATT A 31

( 2 ) INFORMATION FOR SEQ ID NO:16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:16:

TAATACGACT CACTATAG 18

( 2 ) INFORMATION FOR SEQ ID NO:17:

( i ) SEQUENCE CHARACTERISTICS:
        ( A ) LENGTH: 58 base pairs
        ( B ) TYPE: nucleic acid
        ( C ) STRANDEDNESS: double
        ( D ) TOPOLOGY: linear ( i i ) MOLECULE TYPE: cDNA (iii) HYPOTHETICAL: NO (iv) ANTI-SENSE: NO (xi) SEQUENCE DESCRIPTION: SEQ ID NO:17:

CTCTAGATCT CGAGACTAAC ATAGGTCTTA ACTTGACTAA CATCGAGGCC TGCTAGAG                58

(2) INFORMATION FOR SEQ ID NO:18:

(i) SEQUENCE CHARACTERISTICS:
    (A) LENGTH: 8 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:18:

GGGAATTC                8

(2) INFORMATION FOR SEQ ID NO:19:

(i) SEQUENCE CHARACTERISTICS:
    (A) LENGTH: 50 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:19:

CCCGAGGATC ACCAGCAATA TTCCAAAGTA GCATGACAAA AATCTTGGCC                50

(2) INFORMATION FOR SEQ ID NO:20:

(i) SEQUENCE CHARACTERISTICS:
    (A) LENGTH: 22 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:20:

CCCCCTTGAC GACATCCCGA TC                22

(2) INFORMATION FOR SEQ ID NO:21:

(i) SEQUENCE CHARACTERISTICS:
    (A) LENGTH: 42 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO ( x i ) SEQUENCE DESCRIPTION: SEQ ID NO:21:

GGAAGCACAT TGTACTGATA TCTAATCCCT GGTGGTCTCA TA    42

( 2 ) INFORMATION FOR SEQ ID NO:22:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:22:

GTGTGTGTGT AAGATGTTCA GCCTGATCTC TTACCTGTCC TATAATTTTC G    51

( 2 ) INFORMATION FOR SEQ ID NO:23:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:23:

AATTCGAAAA TTATAGGACA GGTAAGAGAT CAGGCTGAAC ATCTTACACA CACAC    55

( 2 ) INFORMATION FOR SEQ ID NO:24:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:24:

GGGCGGTCGC GCGAAAAAGA TGTTCAGCCT GATCTCTTAC CTGTCCTATA ATTTTCG    57

( 2 ) INFORMATION FOR SEQ ID NO:25:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:25:

AATTCGAAAA TTATAGGACA GGTAAGAGAT CAGGCTAACA TCTTTTTCGC GCGACCGCCC    60

( 2 ) INFORMATION FOR SEQ ID NO:26:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: RNA (genomic)

( i i i ) HYPOTHETICAL: NO ( i v ) ANTI-SENSE: NO ( x i ) SEQUENCE DESCRIPTION: SEQ ID NO:26:

GUGUGUGUGU    10

( 2 ) INFORMATION FOR SEQ ID NO:27:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: RNA (genomic)

( i i i ) HYPOTHETICAL: NO ( i v ) ANTI-SENSE: NO ( x i ) SEQUENCE DESCRIPTION: SEQ ID NO:27:

GGGCGGUCGC GCGAAA    16

( 2 ) INFORMATION FOR SEQ ID NO:28:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:28:

AATTCTATGT GATATCAGCT AGTTGGTGGG GTAAAGGCCT    40

( 2 ) INFORMATION FOR SEQ ID NO:29:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:29:

AATTAGGCCT TTACCCCACC AACTAGCTGA TATCACATAG    40

( 2 ) INFORMATION FOR SEQ ID NO:30:

( i ) SEQUENCE CHARACTERISTICS:

(A) LENGTH: 36 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:30:

TACACCGCTA TAAACCCGTA GGCTCATTGC AATTTC     36

(2) INFORMATION FOR SEQ ID NO:31:

(i) SEQUENCE CHARACTERISTICS:
(A) LENGTH: 89 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:31:

AATTCTTTAA AAAATCATAG GACAGGTAAG AGATCAAGCT GAACATCTTG GAGGGACTGT     60

CAGGACAAAA GGGAACCCCC CTTCGGGGG     89

(2) INFORMATION FOR SEQ ID NO:32:

(i) SEQUENCE CHARACTERISTICS:
(A) LENGTH: 90 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:32:

GTGACCCCCC GAAGGGGGGT TCCCTTTTGT CCTGACAGTC CCTCCAAGAT GTTCAGCTTG     60

ATCTCTTACC TGTCCTATGA TTTTTAAAG     90

(2) INFORMATION FOR SEQ ID NO:33:

(i) SEQUENCE CHARACTERISTICS:
(A) LENGTH: 117 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:33:

TACCAGGTAA TATACCACAA CGTGTGTTTC TCTGGTTGAC TTCTCTGTTT GGGGGGGAGA     60

CAGCAGTACA AATGGCAGTA TTCATCCACA ATTTTCCCTA TAGTGAGTCG TATTAAT     117

(2) INFORMATION FOR SEQ ID NO:34:

( i ) SEQUENCE CHARACTERISTICS:
( A ) LENGTH: 4 base pairs
( B ) TYPE: nucleic acid
( C ) STRANDEDNESS: single
( D ) TOPOLOGY: linear ( i i ) MOLECULE TYPE: RNA (genomic)

( i i i ) HYPOTHETICAL: NO ( i v ) ANTI-SENSE: NO ( x i ) SEQUENCE DESCRIPTION: SEQ ID NO:34:

UGAC  4

( 2 ) INFORMATION FOR SEQ ID NO:35:

( i ) SEQUENCE CHARACTERISTICS:
( A ) LENGTH: 6 base pairs
( B ) TYPE: nucleic acid
( C ) STRANDEDNESS: single
( D ) TOPOLOGY: linear ( i i ) MOLECULE TYPE: RNA (genomic)

( i i i ) HYPOTHETICAL: NO ( i v ) ANTI-SENSE: NO ( x i ) SEQUENCE DESCRIPTION: SEQ ID NO:35:

CUGUUU  6

( 2 ) INFORMATION FOR SEQ ID NO:36:

( i ) SEQUENCE CHARACTERISTICS:
( A ) LENGTH: 76 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:36:

GTGACCCCCC AGGGGGTTC CCNNNNNGTC NNNNNNCATC CCAAGATGTT CAGCTTGATC  60

TCTTACCTGT CCTATG  76

( 2 ) INFORMATION FOR SEQ ID NO:37:

( i ) SEQUENCE CHARACTERISTICS:
( A ) LENGTH: 77 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:37:

AATTCATAGG ACAGGTAAGA GATCAAGCTG AACATCTTGG GATGNNNNNN GACNNNNNGG  60

GAACCCCCCT TCGGGGG  77

( 2 ) INFORMATION FOR SEQ ID NO:38:

( i ) SEQUENCE CHARACTERISTICS:
    ( A ) LENGTH: 5 base pairs
    ( B ) TYPE: nucleic acid
    ( C ) STRANDEDNESS: single
    ( D ) TOPOLOGY: linear ( i i ) MOLECULE TYPE: RNA (genomic)

( i i i ) HYPOTHETICAL: NO ( i v ) ANTI-SENSE: NO ( x i ) SEQUENCE DESCRIPTION: SEQ ID NO:38:

AUGAA 5

( 2 ) INFORMATION FOR SEQ ID NO:39:

( i ) SEQUENCE CHARACTERISTICS:
    ( A ) LENGTH: 95 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:39:

GTGACCCCCC GAAGGGGGGT TCCCATGAAG TCNNNNNNAA GATGTTCAGC TTGATCTCTT 60

ACTTGTTCTA AGGTAAGAGA ATTCGGGCCC GGTAC 95

( 2 ) INFORMATION FOR SEQ ID NO:40:

( i ) SEQUENCE CHARACTERISTICS:
    ( A ) LENGTH: 86 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:40:

CGGGCCCGAA TTCTCTTACC TTAGAACAAG TAAGAGATCA AGCTGAACAT CTTNNNNNNG 60

ACTTCATGGG AACCCCCTT CGGGGG 86

( 2 ) INFORMATION FOR SEQ ID NO:41:

( i ) SEQUENCE CHARACTERISTICS:
    ( A ) LENGTH: 6 base pairs
    ( B ) TYPE: nucleic acid
    ( C ) STRANDEDNESS: single
    ( D ) TOPOLOGY: linear ( i i ) MOLECULE TYPE: RNA (genomic)

( i i i ) HYPOTHETICAL: NO ( i v ) ANTI-SENSE: NO ( x i ) SEQUENCE DESCRIPTION: SEQ ID NO:41:

CAUUAC 6

( 2 ) INFORMATION FOR SEQ ID NO:42:

( i ) SEQUENCE CHARACTERISTICS:
    ( A ) LENGTH: 6 base pairs
    ( B ) TYPE: nucleic acid
    ( C ) STRANDEDNESS: single
    ( D ) TOPOLOGY: linear ( i i ) MOLECULE TYPE: RNA (genomic)

( i i i ) HYPOTHETICAL: NO ( i v ) ANTI-SENSE: NO ( x i ) SEQUENCE DESCRIPTION: SEQ ID NO:42:

UUUACG 6

( 2 ) INFORMATION FOR SEQ ID NO:43:

( i ) SEQUENCE CHARACTERISTICS:
    ( A ) LENGTH: 5 base pairs
    ( B ) TYPE: nucleic acid
    ( C ) STRANDEDNESS: single
    ( D ) TOPOLOGY: linear ( i i ) MOLECULE TYPE: RNA (genomic)

( i i i ) HYPOTHETICAL: NO ( i v ) ANTI-SENSE: NO ( x i ) SEQUENCE DESCRIPTION: SEQ ID NO:43:

UUYRC 5

( 2 ) INFORMATION FOR SEQ ID NO:44:

( i ) SEQUENCE CHARACTERISTICS:
    ( A ) LENGTH: 111 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:44:

TACCAGGTAA TATACCACAA CGTGTGTTTC TCTGGTATGA TTCTCATTAC GAGACAGCAG 60

TACAAATGGC AGTATTCATC CACAATTTTC CCTATAGTGA GTCGTATTAA T 111

( 2 ) INFORMATION FOR SEQ ID NO:45:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:45:

ATTAATACGA CTCACTATAG GG 22

( 2 ) INFORMATION FOR SEQ ID NO:46:

( i ) SEQUENCE CHARACTERISTICS:

( A ) LENGTH: 92 base pairs
        ( B ) TYPE: nucleic acid
        ( C ) STRANDEDNESS: single
        ( D ) TOPOLOGY: linear ( i i ) MOLECULE TYPE: mRNA ( i i i ) HYPOTHETICAL: NO ( i v ) ANTI-SENSE: NO ( x i ) SEQUENCE DESCRIPTION: SEQ ID NO:46:

GGGAAAAUUG UGGAUGAAUA CUGCCAUUUG UACUGCUGUC UCGUAAUGAG AAUCAUACCA        60

GAGAAACACA CGUUGUGGUA UAUUACCUGG UA        92

( 2 ) INFORMATION FOR SEQ ID NO:47:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:47:

GAGCTCGAAT TCACTGGCCG TC        22

( 2 ) INFORMATION FOR SEQ ID NO:48:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:48:

CCCCCCGGCG CCTTATTAAT ACGACTCACT ATAGGGCATT CGCCATTCAG GCTG        54

( 2 ) INFORMATION FOR SEQ ID NO:49:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:49:

NNNNU Y NNNN        10

( 2 ) INFORMATION FOR SEQ ID NO:50:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear (i i) MOLECULE TYPE: RNA (genomic)

(x i) SEQUENCE DESCRIPTION: SEQ ID NO:50:

NNNNUHNNNN                                                                 10